United States Patent
Venkataramani et al.

(10) Patent No.: US 11,493,499 B1
(45) Date of Patent: Nov. 8, 2022

(54) EVENT TIMING DETECTION FOR DNA SEQUENCING

(71) Applicant: Seagate Technology LLC, Cupertino, CA (US)

(72) Inventors: Raman Venkataramani, Longmont, CO (US); William Radich, Longmont, CO (US)

(73) Assignee: Seagate Technology LLC, Cupertino, CA (US)

(*) Notice: Subject to any disclaimer, the term of this patent is extended or adjusted under 35 U.S.C. 154(b) by 988 days.

(21) Appl. No.: 16/175,223

(22) Filed: Oct. 30, 2018

(51) Int. Cl.
| | |
|---|---|
| G01N 27/447 | (2006.01) |
| G01N 27/327 | (2006.01) |
| G01N 33/487 | (2006.01) |
| B82Y 15/00 | (2011.01) |
| G06K 9/62 | (2022.01) |

(52) U.S. Cl.
CPC ..... *G01N 33/48721* (2013.01); *G01N 27/447* (2013.01); *B82Y 15/00* (2013.01); *G06K 9/6273* (2013.01)

(58) Field of Classification Search
CPC ........... G01N 33/48721; G01N 27/447; B82Y 15/00; G06K 9/6273
See application file for complete search history.

(56) References Cited

U.S. PATENT DOCUMENTS

| | | | |
|---|---|---|---|
| 8,370,079 B2 | 2/2013 | Sorenson et al. | |
| 8,452,546 B1 * | 5/2013 | Lathrop | G01N 33/48721 435/6.1 |
| 2009/0029477 A1 | 1/2009 | Meller et al. | |
| 2010/0122907 A1 | 5/2010 | Stanford et al. | |
| 2010/0331194 A1 | 12/2010 | Turner et al. | |
| 2011/0008775 A1 | 1/2011 | Gao et al. | |
| 2012/0193236 A1 | 8/2012 | Peng et al. | |
| 2013/0071837 A1 | 3/2013 | Winters-Hilt et al. | |
| 2013/0244340 A1 | 9/2013 | Davis et al. | |
| 2013/0264207 A1 | 10/2013 | Ju et al. | |
| 2013/0317755 A1 | 11/2013 | Mishra et al. | |

(Continued)

OTHER PUBLICATIONS

Schreiber et al., "Segmentation of noisy Signals Generated By a Nanopore," bioRxiv—The Preprint Server For Biology, Cold Spring Harbor Laboratory, Jan. 23, 2015 bioRxiv preprint doi: https://doi.org/10.1101/014258 (Year: 2015).*

(Continued)

*Primary Examiner* — Alexander S Noguerola
(74) *Attorney, Agent, or Firm* — Christian W. Best

(57) ABSTRACT

Systems and methods are disclosed for performing event timing detection for DNA sequencing. In certain embodiments, a method may comprise generating a signal based on a DNA strand passed through a nanopore sensor, sampling the signal to generate a plurality of sample values, and detecting one or more event boundaries based on the sample values, an event representing a movement of a single DNA base of the DNA strand through the nanopore sensor. Detecting the one or more event boundaries may include segmenting the plurality of sample values into multiple events to calculate an optimal total score, assigning an event value to a selected event from the multiple events based on sample values of the selected event, and providing the event value to a base caller to determine a sequence of DNA bases.

20 Claims, 17 Drawing Sheets

(56) References Cited

U.S. PATENT DOCUMENTS

2018/0340220 A1 11/2018 Merriman et al.
2021/0035656 A1 2/2021 Venkataramani et al.

OTHER PUBLICATIONS

Kevin Karplus, slide set entitled "Segmentation and HMMs for nanopore data," Nov. 6, 2014 Downloaded from https://users.soe.ucsc.edu/~karplus/papers/segmentation-2014-nov-6.pdf (Year: 2014).*
Liang et al., "Bayesian Basecalling for DNA Sequence Analysis using Hidden Markov Models," Jul. 2007, IEEE/ACM transactions on computational biology and bioinformatics/ IEEE, Acm 4(3):430-40 (Year: 2007).*
Turakhia et al., "Darwin: A Genomics Co-Processor Provides up to 15,000x acceleration on long read assembly," Session 3A-Programmable Devices and Co-processors, ASPLOS'18, Mar. 24-28, 2018, Williamsburg, VA USA (Year: 2018).*
A. H. Laszlo, et al., "Decoding long nanopore sequencing reads of natural DNA," Nature biotechnology, vol. 32, No. 8, p. 829, 2014.
G. F. Schneider et al, "DNA sequencing with nanopores," Nature biotechnology, vol. 30, No. 4, p. 326, 2012.
I. M. Derrington, et al., "Nanopore DNA sequencing with MspA," Proceedings of the National Academy of Sciences, vol. 107, No. 37, pp. 16 060-16 065, 2010.
Boza et al.; "DeepNano: Deep recurrent neural networks for base calling in MinION nanopore reads," PLoS ONE 12 (6): e0178751. https://doi.org/10.1371/journal.pone.0178751; 2017; 13 pages.
David et al; Nanopore sequencing data, The Author 2016; Bioinformatics, 33(1), 2017, 49-55; doi: 10.1093/bioinformatics/btw569; Advance Access Publication Date: Sep. 10, 2016; 7 pages.

Deamer, et al.; "Nanopores and nucleic acids: prospects for ultrarapid sequencing," TIBTECH Apr. 2000 (vol. 18); 2000 Elsevier Science Ltd.; 5 pages.
Derrington et al.; "Nanopore DNA sequencing with MspA," www.pnas.org/cgi/doi/10.1073/pnas.1001831107; PNAS; Sep. 14, 2010; vol. 107, No. 37; 6 pages.
Durbin et al.; "Biological sequence analysis: Probabilistic models of proteins and nucleic acids," Cambridge University Press; 366 pages.
Jain et al.; "The Oxford Nanopore MinION: delivery of nanopore sequencing to the genomics community," Genome Biology (2016) 17:239, DOI 10.1186/s13059-016-1103-0; 11 pages.
Loman, et al., "A complete bacterial genome assembled de novo using only nanopore sequencing data"; http://dx.doi.org/10.1101/015552; Feb. 20, 2015.
Maxam, et al.; "A new method for sequencing DNA"; Proc. Natl. Acad. Sci. USA vol. 74, No. 2, pp. 560-564, Feb. 1977; 5 pages.
Sanger et al.; "DNA Sequencing with chain-terminating inhibitors," Proc. Natl. Acad. Sci. USA, vol. 74, No. 12, pp. 5463-5467, Dec. 1977; 5 pages.
Schneider et al.; "DNA sequencing with nanopores," vol. 30, No. 4 Apr. 2012 Nature Biotechnology; 3 pages.
Stoiber et al.; "BasecRAWller: Streaming Nanopore Basecalling Directly from Raw Signal," http://dx.doi.org/10.1101/133058; May 1, 2017; 15 papges.
Teng et al.; Chiron: Translating nanopore raw signal directly into nucleotide sequence using deep learning, http://dx.doi.org/10.1101/179531; Aug. 23, 2017; 10 pages.
Zhang et al.; "The Role of Contacts in Long-Range Protein Conductance," Submitted to Proceedings of the National Academy of Sciences of the United States of America; 6 pages.

* cited by examiner

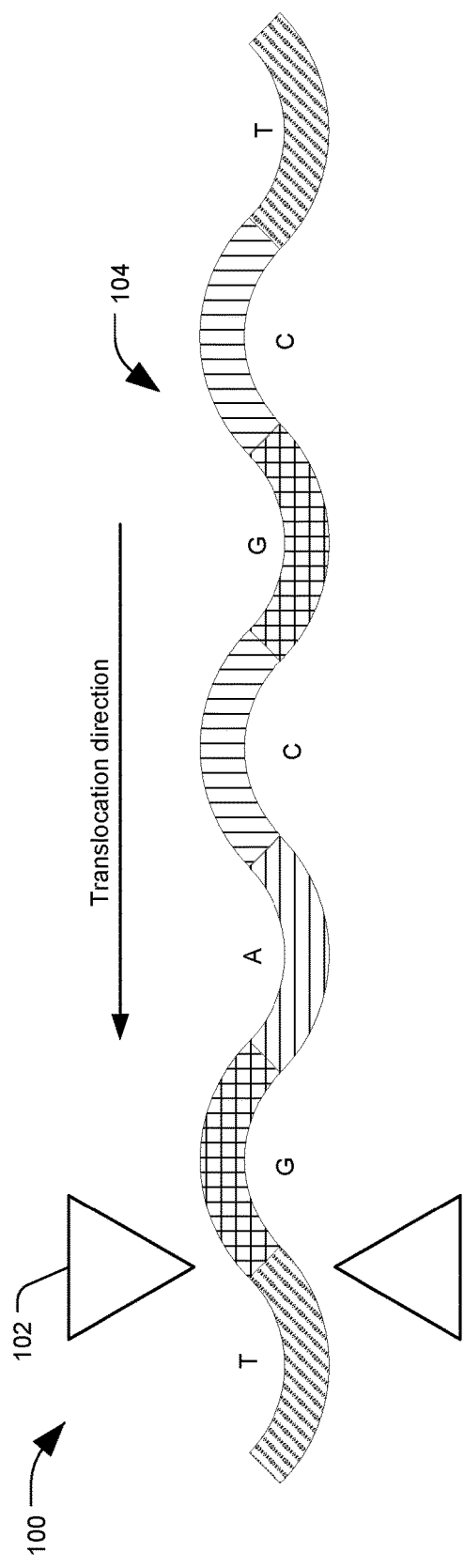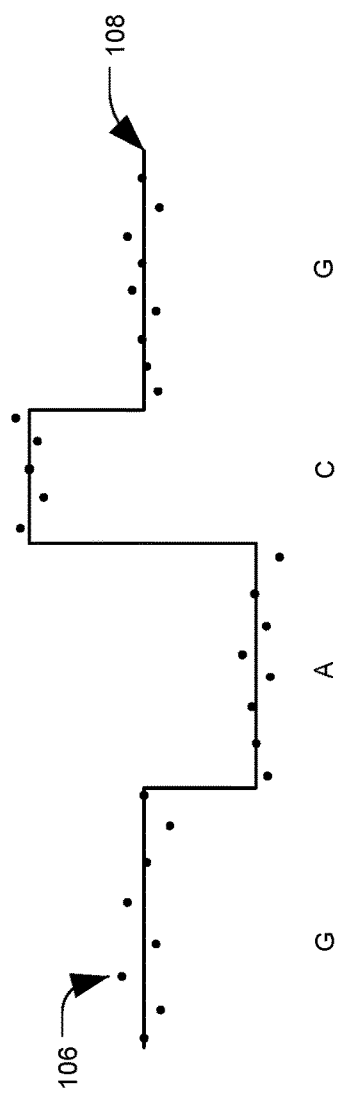
FIG. 1A
FIG. 1B

EVENT TIMING DETECTION FOR DNA SEQUENCING

SUMMARY

In certain embodiments, a method may comprise generating a signal based on a DNA (deoxyribonucleic acid) strand passed through a nanopore sensor, sampling the signal to generate a plurality of sample values, and detecting one or more event boundaries based on the sample values, an event representing a movement of a single DNA base of the DNA strand through the nanopore sensor. Detecting the one or more event boundaries may include segmenting the plurality of sample values into multiple events to calculate an optimal total score, assigning an event value to a selected event from the multiple events based on sample values of the selected event, and providing the event value to a base caller to determine a sequence of DNA bases.

In certain embodiments, an apparatus may comprise a circuit configured to generate a signal based on a DNA strand passed through a nanopore sensor, sample the signal to generate a plurality of sample values, and detect one or more event boundaries based on the sample values, an event representing a movement of a single DNA base of the DNA strand through the nanopore sensor. Detecting one or more event boundaries may include segmenting the plurality of sample values into multiple events to calculate an optimal total score, assigning an event value to a selected event from the multiple events based on sample values of the selected event, and providing the event value to a base caller to determine a sequence of DNA bases.

In certain embodiments, a memory device may store instructions that, when executed by a processor, cause the processor to perform a method comprising generating a signal based on a DNA strand passed through a nanopore sensor, sampling the signal to generate a plurality of sample values, and detecting one or more event boundaries based on the sample values, an event representing a movement of a single DNA base of the DNA strand through the nanopore sensor. Detecting the one or more event boundaries may include segmenting the plurality of sample values into multiple events to calculate an optimal total score, assigning an event value to each event from the multiple events based on sample values of a corresponding event, and providing the event values to a base caller to determine a sequence of DNA bases.

BRIEF DESCRIPTION OF THE DRAWINGS

FIGS. 1A and 1B are diagrams of a system configured to perform event timing detection for DNA (deoxyribonucleic acid) sequencing, in accordance with certain embodiments of the present disclosure.

DETAILED DESCRIPTION

Figure 2:
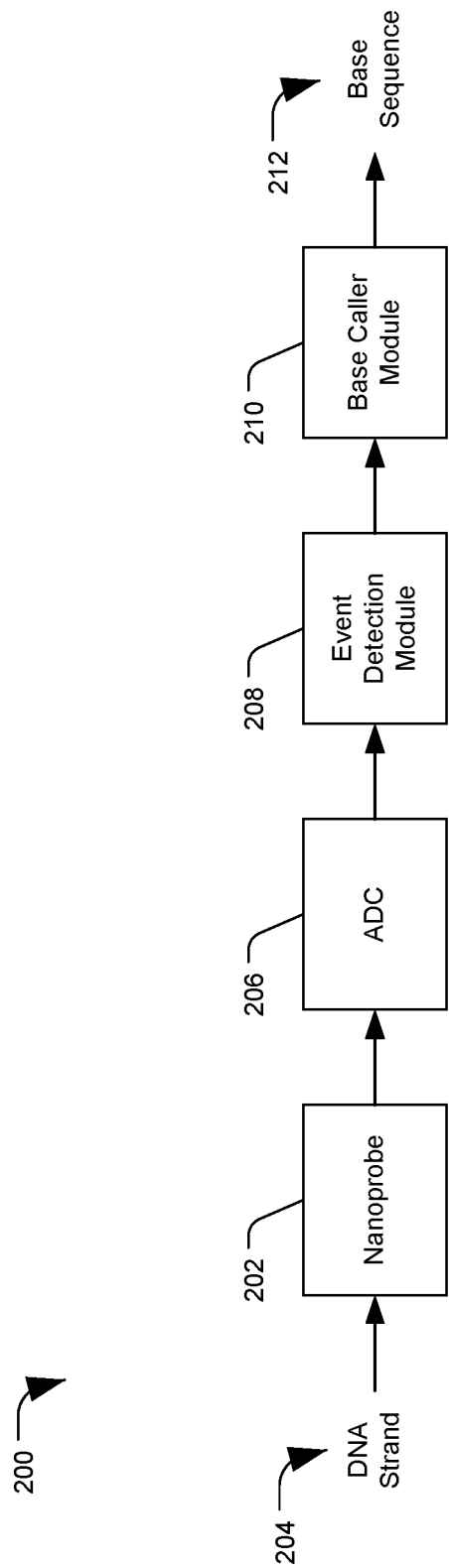
FIG. 2 is a diagram of a system configured to perform event timing detection for DNA sequencing, in accordance with certain embodiments of the present disclosure.

In the following detailed description of certain embodiments, reference is made to the accompanying drawings which form a part hereof, and in which are shown by way of illustration of example embodiments. It is also to be understood that features of the embodiments and examples herein can be combined, exchanged, or removed, other embodiments may be utilized or created, and structural changes may be made without departing from the scope of the present disclosure.

In accordance with various embodiments, the methods and functions described herein may be implemented as one or more software programs running on a computer processor or controller. Dedicated hardware implementations including, but not limited to, application specific integrated circuits, programmable logic arrays, and other hardware devices can likewise be constructed to implement the methods and functions described herein. Methods and functions may be performed by modules, which may include one or more physical components of a computing device (e.g., logic, circuits, processors, etc.) configured to perform a particular task or job, or may include instructions that, when executed, can cause a processor to perform a particular task or job, or any combination thereof. Further, the methods described herein may be implemented as a computer readable storage medium or memory device including instructions that, when executed, cause a processor to perform the methods.

FIG. 1A is a diagram of a system, generally designated 100, configured for event timing detection for DNA (deoxyribonucleic acid) sequencing, in accordance with certain embodiments of the present disclosure. The system 100 may include a nanopore sensor 102 (sometimes called a nanoprobe, nanopore channel, or just "pore") through which a DNA strand 104 may be passed. The DNA strand 104 may be a single-stranded DNA (ssDNA) that consists of only one chain of nucleotides rather than the two base-pairing strands found in DNA in the double-helix form. The DNA strand 104 may include a sequence of nucleobases or just "bases", nitrogen-containing biological compounds that form nucleosides, which in turn are components of nucleotides, with all of these monomers constituting the basic building blocks of nucleic acids. In an example embodiment, the DNA strand 104 may include a sequence of bases from the set including adenine (A), cytosine (C), guanine (G), and thymine (T).

As the DNA strand 104 passes through the sensor 102, the sensor may detect changes in the DNA strand 104 that indicate the timing of events along the DNA strand 104. An "event" may be defined as the movement of a single base through the nanopore channel 102.

DNA sequencing has undergone several phases of innovation starting from two the classic sequencing methods of Sanger dideoxy (terminator base) method and the Maxam-Gilbert (chemical cleavage) method. Both methods are similar in that they generate short DNA fragments (of random lengths) terminating at an instance of a selected base. A technique called polyacrylamide gel electrophoresis is used to measure the lengths of the resulting fragments, which tells us the positions of the specific base in the original DNA strand. The process is done separately for each of the four bases to get the complete DNA sequence. A limitation of these methods is that they only work well for sequences that no longer than 100 bases. Beyond this limit the uncertainty in the position of each base becomes unacceptable. Longer sequences had to be broken down, sequenced individually, and stitched together like pieces of a jigsaw puzzle using genome assembly algorithms. The second generation of DNA sequencing saw the rise of massively parallel sequencers that were still limited to processing short fragments. The idea of "single molecule sequencing" is to avoid fragmentation of the DNA and try to sequence the entire ssDNA molecule in a single pass. Aside from its usefulness in medicine, DNA sequencing is also of interest to researchers in archival data storage due to the high density and long life of DNA when stored in the right conditions.

Nanopore DNA sequencing can provide for low-cost high-throughput DNA genome sequencing. As described above, a nanopore DNA sequencing device, which may include system 100, may contains a tiny pore 102 through which a negatively charged ssDNA 104 translocates under an external electric field by a process called electrophoresis. The width of the nanopore channel 102 may be in the order of 2 nm, just wide enough for an ssDNA molecule to pass through. The raw signal from the device sensor 102 may be an oversampled transverse ionic or tunneling current between two electrodes. Each type of base (labeled T, G, A, C) may produce a characteristic current response. The signal samples can be modeled as piecewise constants over each event.

Thus, by measuring the changes in the measured current with the passing of each base in the DNA sequence 104 through the pore 102, the system 100 can detect the bases (or nucleotides) in the ssDNA sequence 104.

FIG. 1B depicts an example readout signal spanning four events as the ssDNA strand 104 passes through the sensor 102. The dots 106 may represent oversampled current samples, while the line 108 may represents an ideal "level" corresponding to each event.

As the DNA strand 104 passes through the sensor 102 in the translocation direction indicated in FIG. 1A, the base labeled "G" will be sampled. The sensor 102 generates a current as the DNA strand 104 passes through, and sample values are taken from the current at periodic intervals. The sample values may be indicated by the dots 106 of FIG. 1B. The values of samples 106 taken from a same base can vary slightly due to various factors. The process may continue as the bases A, C, and another G pass through the sensor 102. A sequence of signal "levels" may be determined based on the sample values 106, which levels may be indicated by the horizontal sections of the line 108. The levels may be used to identify individual events, and potentially to identify the bases that correspond to each level.

One main problem associated with nanopore DNA sequencing may be using the raw current signal to recover the underlying DNA base sequence (which may be called the "base calling problem"). As noted above, various factors can cause individual samples from a same event to vary slightly from each other. Likewise, as a sequence of bases are sampled, the same type of base (e.g. the base "G" may produce different signal "levels" as different points along an ssDNA strand 104. Therefore, even if there are only four types of bases in the ssDNA strand 104, there may a continuum of levels that may be produced during sequencing (e.g., which continuum may be divided into a large number of discrete levels, such as ninety or more). Further, variation in the translocation speed means the number of samples that may be obtained for each event (sometimes called the "run length" of an event) is unknown, and therefore the duration of each event is uncertain. Identifying which bases correspond to which signal samples may be a difficult problem.

However, it may often be simpler to first identify events boundaries (which may be called the "event detection problem"), and post process the identified events to recover the base sequence. A system configured to perform event timing detection is shown in greater detail in FIG. 2.

FIG. 2 is a diagram of a system, generally designated 200, configured to perform event timing detection for DNA sequencing, in accordance with certain embodiments of the present disclosure. In particular, FIG. 2 depicts an example DNA sequencer, including a number of processing blocks, modules, or system components configured to perform signal processing, event detection, and DNA sequencing. The system 200 may include a nanoprobe 202, an analog to digital converter (ADC) 206, an event detection module 208, and a base caller module 210. The processing blocks may be included on or executed by one or more modules or physical components of a signal processing channel circuit.

The nanoprobe 202 may correspond to the nanopore sensor of FIG. 1A. A DNA strand 204 may be passed through the nanoprobe 202, and the nanoprobe may generate an analog signal from sensing the DNA strand 204. The signal may be passed to the ADC 206, which may periodically sample the analog signal to generate a sequence of digital sample values. For example, the sample values may represent a voltage of the signal at the point in time that the signal was sampled. The digital sample values may be passed to the event detection module 208. The event detection module 208 may perform the processes and methods described herein to associate the sample values into individual events, for example by determining a run-length of each event. The event detection module may also assign a level to each determined event, for example based on an average sample value for samples in the determined event. The base caller module 210 may determine a DNA base sequence based on the detected event boundaries, and potentially the levels assigned to each event. The base-caller may typically be implemented using hidden Markov models (HMM) or neural-networks. In some implementations, event detection and base-calling could be performed jointly, for example based on the digital sample values or the raw signal from the nanoprobe 202.

As discussed above, the event detection module 208 may perform a pre-processing step to convert a sequence of signal samples into a sequence of events which can then be fed to the base-caller module 210.

Some approaches to event detection first apply an algorithm to attempt to find the location of an event boundary (e.g. a level transition) in the input sequence and then recursively apply the algorithm to each sub-segment. The most likely boundary location may be found using a Bayesian criterion with a somewhat crude assumption the entire signal consists of only two events. At best, such a divide and conquer algorithm has O(N log N) computational complexity for an input of length N. This is a high level of computational complexity that may be unsuitable for real-time sequencing implementation for long reads. A superior approach would be a method with linear complexity in N that is more amenable to real-time implementation.

Below are described some basic signal and noise models used to model a nanopore DNA sequencer and a simple approach of using a hidden Markov model (HMM) to track the signal levels and perform event detection. The readout current signal may be modeled as a (noisy) piecewise-constant over each event. Formally, the observed samples may be normally distributed with mean $\lambda$ and noise variance $\sigma^2$:

$$s_n \sim \mathcal{N}(\lambda, \sigma^2) \qquad (1)$$

where $\lambda \in \Lambda$ is the event level from a discrete set of levels $\Lambda$, and $\sigma^2$ is the noise variance. The event detection problem as follows:

Problem statement: Given observation samples $s=\{s_n: n=1, \ldots, N\}$ what is the best way to segment them into events?

If the possible signal levels are known, one solution to the problem may include using an HMM to keep track of the signal level of the current event. An example HMM for level-based event segmentation is described in regard to FIG. 3.

Figure 3:
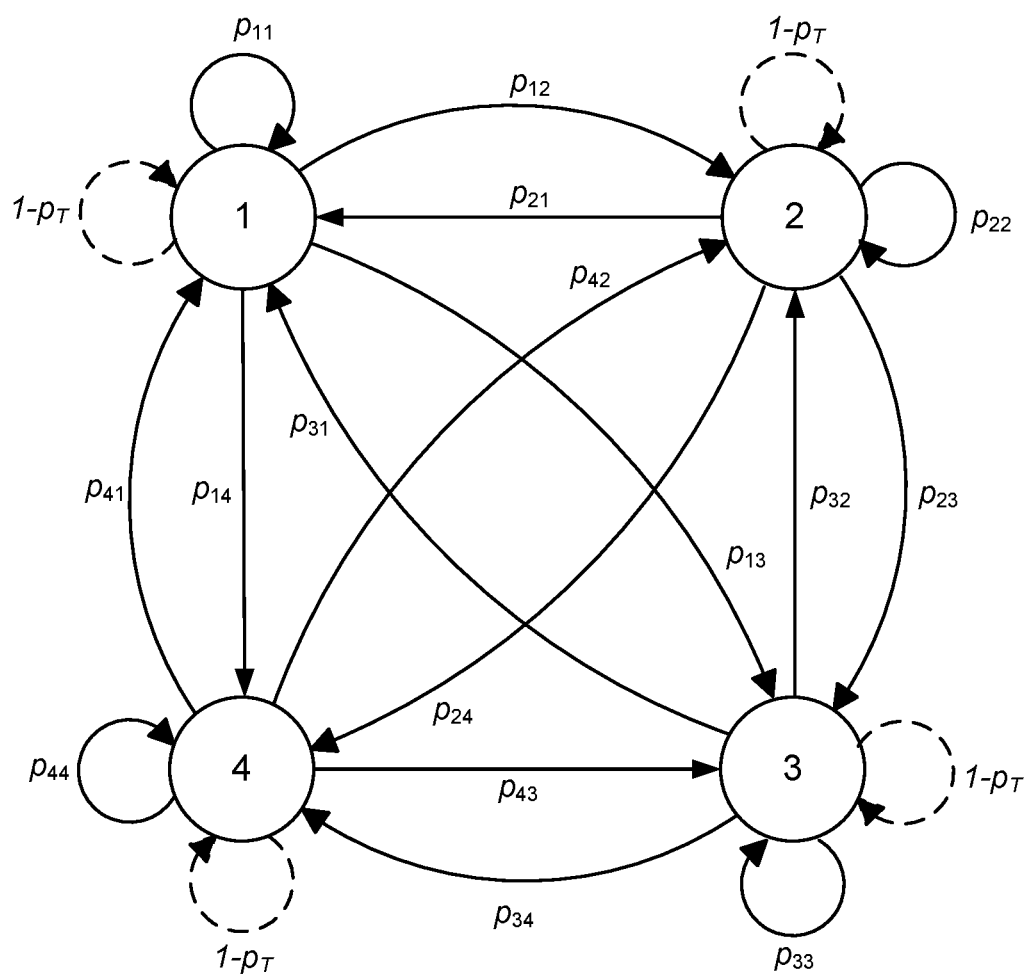
FIG. 3 is a diagram of a system configured to perform event timing detection for DNA sequencing, in accordance with certain embodiments of the present disclosure.

FIG. 3 is a diagram of a system, generally designated 300, configured to perform event timing detection for DNA sequencing, in accordance with certain embodiments of the present disclosure. In particular, FIG. 3 depicts an example level-based hidden Markov model (HMM) 300 for segmenting a sequence of signal samples into separate events using signal levels for the samples.

Each state in the HMM 300 may represent a unique level from the discrete set A, and has an edge to every other state including itself. For example, FIG. 3 depicts a signal level tracking HMM 300, abbreviated as SL-HMM, with a set of four levels or states (labeled "1" through "4"). An edge from state i to another state j≠i (represented in FIG. 3 as solid arrows between different states) represents the end of an event and the beginning of a new event having a different level. There may be two types of self loops, e.g., edges from a state i to itself. The self loops can either represent the continuation of the same event (shown as dashed line arrows), or a transition to a new event without a level change (shown as solid arrows). The HMM state keeps track of the current signal level, but not the exact duration of the current event. A limitation of this model may be that it can model only a geometric distribution for the event duration d with an average of $1/p_T$, e.g., $P(d=l)=p_T(1-p_T)^{l-1}$, where l is the length or duration of an event measured in a number of samples, and $p_T$ represents the total probability of all transitions from the current state via a solid edge.

In general, the individual transition probabilities $p_{ij}$ from state i to state j (e.g. the transition from state 1 to state 2 is labeled as $p_{12}$ in FIG. 3) can be modeled. With the signal model (1), the (log-domain) HMM branch metric ($\beta_n$) at time n ($t_n$) can be calculated as:

$$\beta_n(i \to j, t_n = 1) = -\log p_{ij} + \frac{1}{2\sigma^2}(s_n - \lambda_j)^2 + \frac{1}{2}\log(2\pi\sigma^2),$$

$$\beta_n(i \to i, t_n = 0) = -\log(1 - p_T) + \frac{1}{2\sigma^2}(s_n - \lambda_i)^2 + \frac{1}{2}\log(2\pi\sigma^2).$$

The Viterbi algorithm can be used to efficiently find the maximum likelihood (ML) path, which may be the path with the lowest accumulated path metric through the HMM. This path provides a segmentation of the raw signal into events. A typical path (state sequence) through the example HMM 300 is depicted in FIG. 4.

Figure 4:
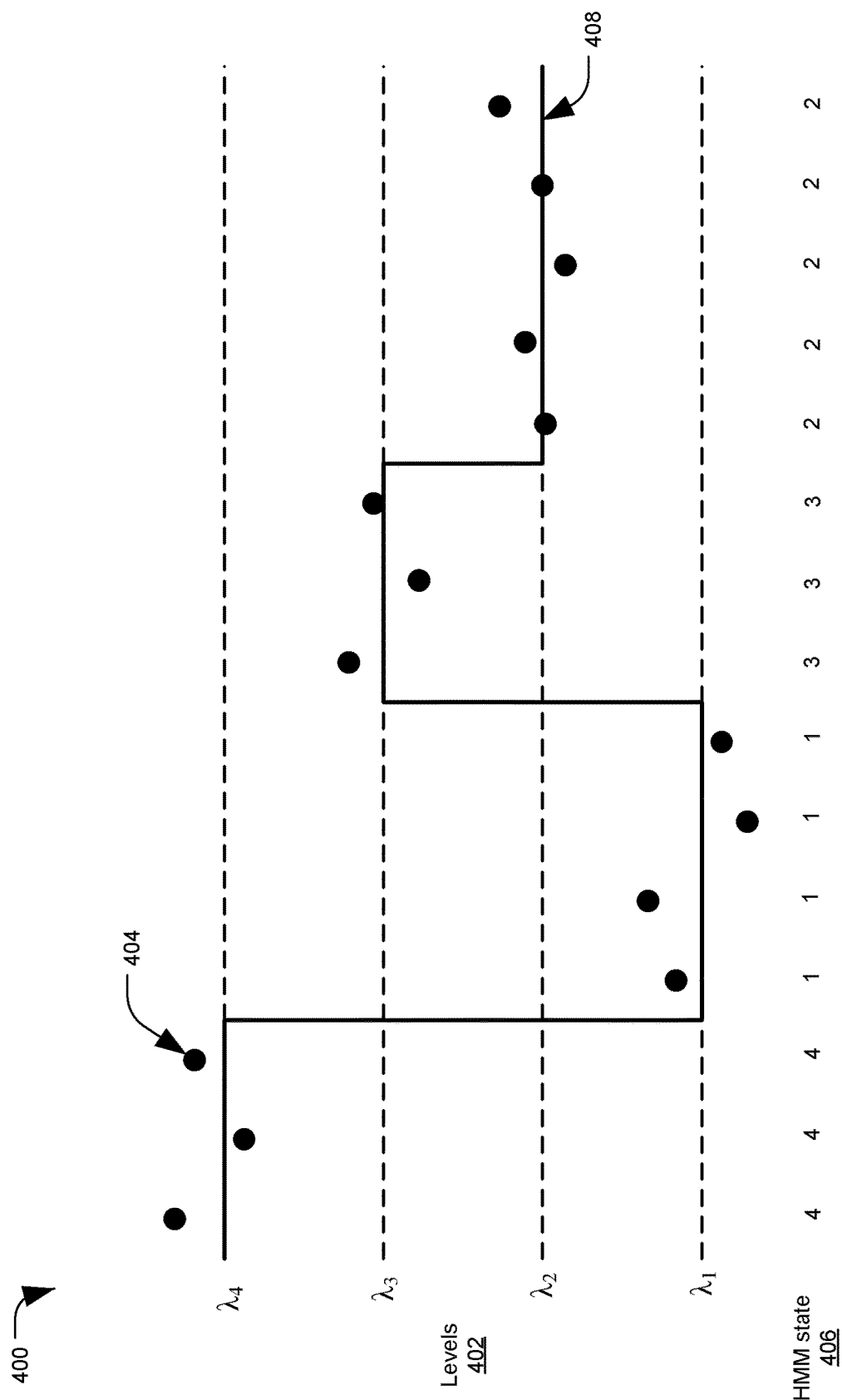
FIG. 4 is a diagram illustrating the input and output signals in event timing detection for DNA sequencing, in accordance with certain embodiments of the present disclosure.

FIG. 4 is a diagram of input and output signals, generally designated 400, illustrating the event timing detection for DNA sequencing, in accordance with certain embodiments of the present disclosure. In particular, FIG. 4 shows an example path (state sequence) through an HMM with four discrete levels, such as the MINI 300 of FIG. 3.

The levels 402 may be identified as $\lambda_1$ through $\lambda_4$. The dots 404 may represent individual samples taken from the measured signal, with their y-position on the chart indicating the signal value of that particular sample. The solid line may indicate which levels 402 that each sequence of samples 404 correspond to according to the HMM states 406. A new event may begin whenever the HMM state 406 changes by moving to another level index 402. However, in some instances, a new event may begin at the same HMM state 406 and level 402. For example, if the four levels 402 corresponded to four different DNA bases, there may be two consecutive bases of the same type, which may result in a new event that shared a same level 402 and HMM state 406 as the previous event. However, in practice it may be difficult to model the four DNA bases with only four discrete levels 402 and four HMM states 406, as various factors such as inter-symbol interference (ISI) can influence the signal samples, resulting in the need for many more levels and states.

The SL-HMM approach may be practical if A is a small set of known discrete levels. In particular, suppose that there is very low inter-symbol interference (ISI) in the event level response to the base sequence, e.g., if the event levels are dependent on only one base at a time. Then, A may contain only four known levels corresponding to the four bases A, C, G, and T. In such an embodiment, the Viterbi algorithm may directly produce both the event boundaries and the underlying base sequence. However, since the number of levels may grow exponentially with the ISI length, it may become impractical to use the SL-HMM approach when the ISI is strong, as will be shown herein. Example applications of a SL-HMM are described in regard to FIGS. 5 and 6.

Figure 5:
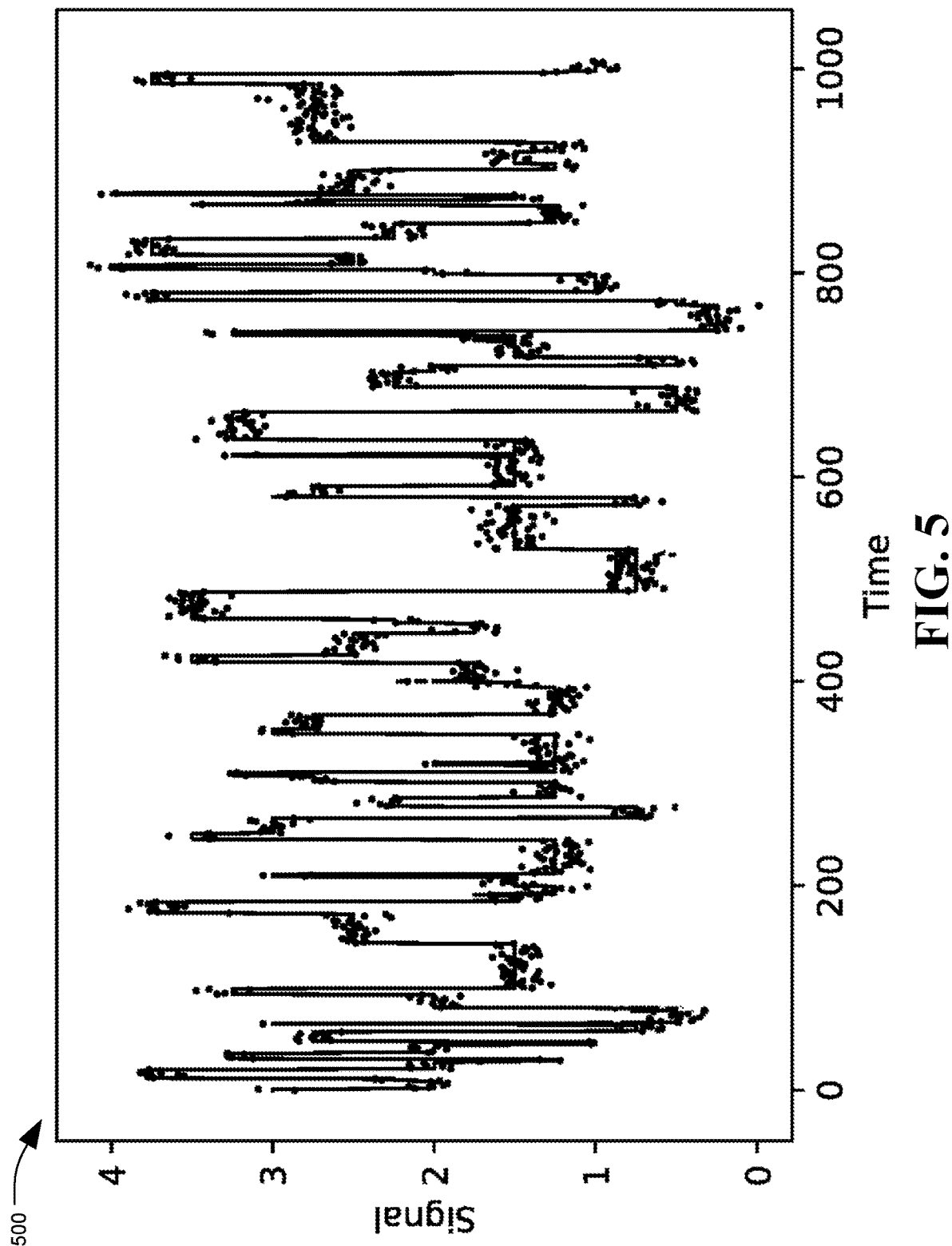
FIG. 5 is a diagram of a chart showing results of an event timing detector for DNA sequencing, in accordance with certain embodiments of the present disclosure.

FIG. 5 is a diagram of a chart, generally designated 500, showing results of an event timing detector for DNA sequencing, in accordance with certain embodiments of the present disclosure. In particular, FIG. 5 shows an example "squiggle plot" generated from the application of a signal level hidden Markov model (SL-HMM) event detection algorithm to a synthetically-generated signal. The signal may have L=16 levels, and the SL-HMM may have a set of discrete HMM levels:

$$\Lambda = \left\{ \frac{1}{4}, \frac{2}{4}, \frac{3}{4}, \ldots \frac{16}{4} \right\}$$

and a noise parameter of σ=0.1. FIG. 5 shows the output of the Viterbi detector applied to the synthetic data. The dots may represent the raw noisy data samples and the lines may represent the detected events.

Figure 6:
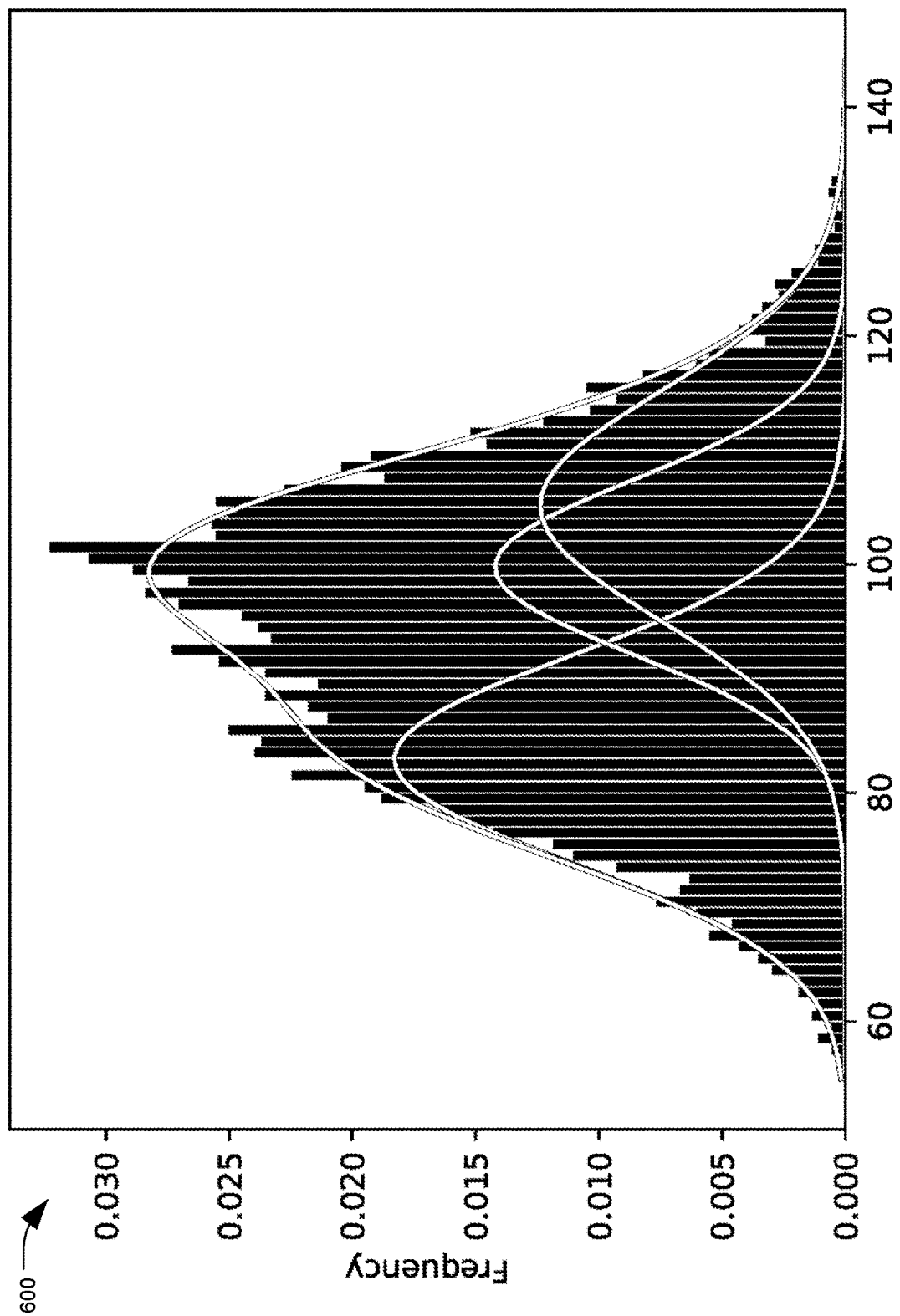
FIG. 6 is a diagram of a chart showing results of an event timing detector for DNA sequencing, in accordance with certain embodiments of the present disclosure.

FIG. 6 is a chart, generally designated 600, showing results of an event timing detector for DNA sequencing, in accordance with certain embodiments of the present disclosure. FIG. 6 depicts the results of a second example, in which the SL-HMM algorithm may be applied an example nanopore signal from an E. coli DNA sample, henceforth "E. coli data set." FIG. 6 shows a histogram of the observed event levels in the data set. In this case the absence of sharp peaks in the histogram indicates that the levels do not come from a small discrete set. In such instances it may be more convenient to model the histogram as a continuous distribution. Here, a Gaussian mixture model with three components (the three lower white "bell curves") was chosen to fit the distribution. The higher white line represents a combination of all the components.

Figure 7:
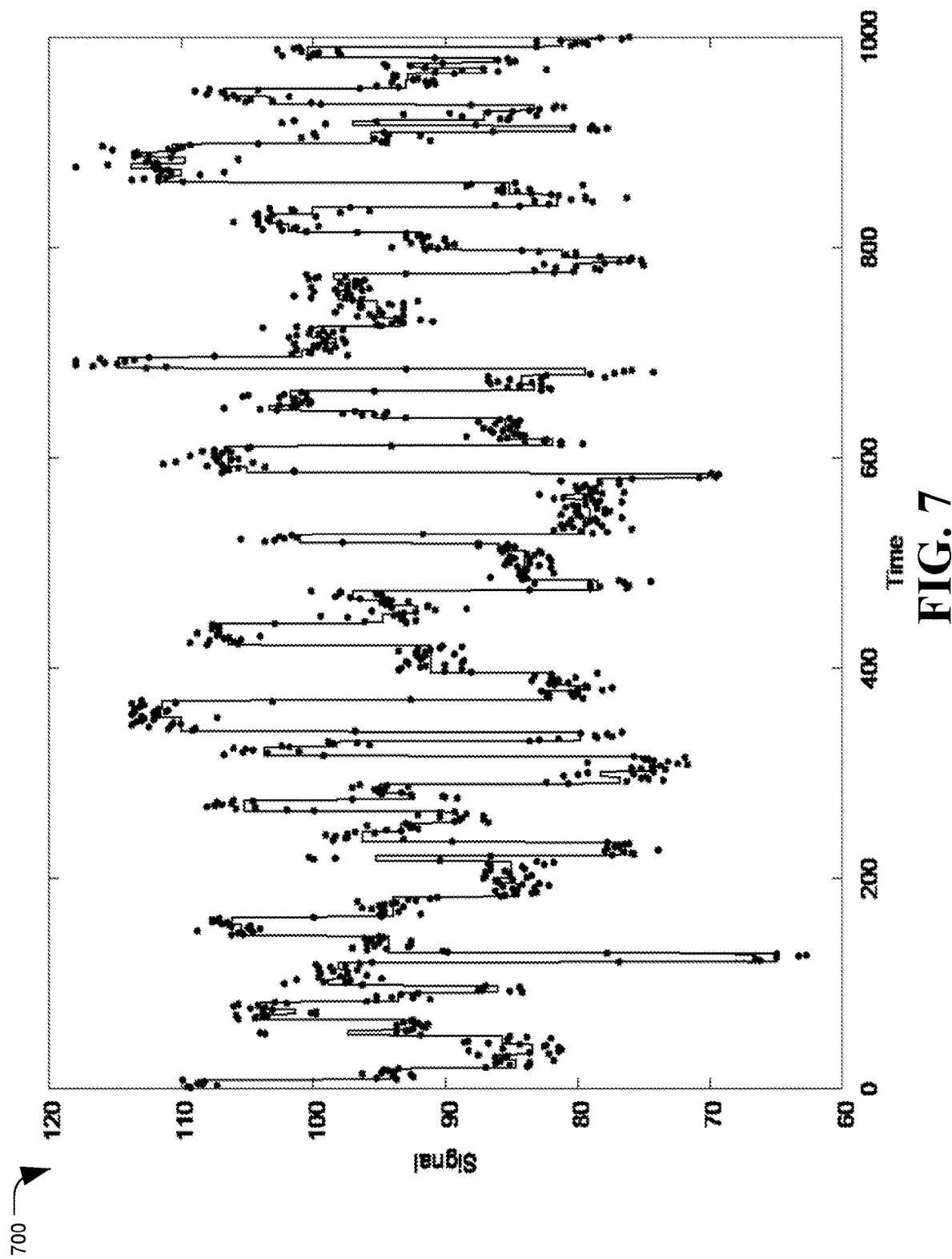
FIG. 7 is a diagram of a chart showing results of an event timing detector for DNA sequencing, in accordance with certain embodiments of the present disclosure.

Since the distribution of the signal levels in the E. coli data set is continuous in the range [55,144], the levels can be approximated by quantizing them to a set of L=90 discrete levels with a step size of 1; e.g., $\Lambda=\{55, 56, \ldots, 144\}$. Since the HMM state diagram may be fully connected (e.g. each state has an edge to every other state and itself), there may be over 8100 edges in the SL-HMM; a very computationally-intensive number. The event transition probability may be estimated to be $p_T=0.1$ for an average dwell time of 10 samples and $$p_{ij}=p_T P(\lambda=\lambda_j)$$

where $P(\lambda=\lambda_i)$ can be obtained from the event level histogram. Finally, the noise standard deviation may be estimated to be σ≈2.5. All the above parameters may be estimated from the labeled data. FIG. 7 shows the output of the Viterbi detector applied to 1000 samples (the "Time" x-axis) of the E. coli data as described in regard to FIG. 6.

The previous example with the E. coli data explained that a signal level tracking HMM (SL-HMM) may contain an enormous number edges and states. In general, if an HMM has L states (e.g. one for each signal level) there may be about $L^2$ edges. Thus, the SL-HMM approach can become impractical for large level sets.

Accordingly, a novel architecture is presented herein for event detection using a "run-length tracking HMM" (RL-HMM). The RL-HMM may be used to perform event detection efficiently even for large level sets, without the quadratic growth of the SL-HMM size. The idea with the RL-HMM is to encode the run-length or duration of the current event (e.g. based on a number of samples), rather than the event signal level, into the HMM state. The event levels may be estimated on-the-fly at each state based on the samples in the current event at that state. Since the signal level does not need to be encoded at all, the RL-HMM method can work accurately for large level sets, or even continuous level sets without level quantization (e.g. when there is a continuous value range rather than discrete levels). For discrete level sets, the RL-HMM method is provably equivalent to the traditional signal level tracking HMM, but with a much lower implementation complexity in practice. An overview of the process of the proposed event segmentation operation is described in regard to FIG. 8.

Figure 8:
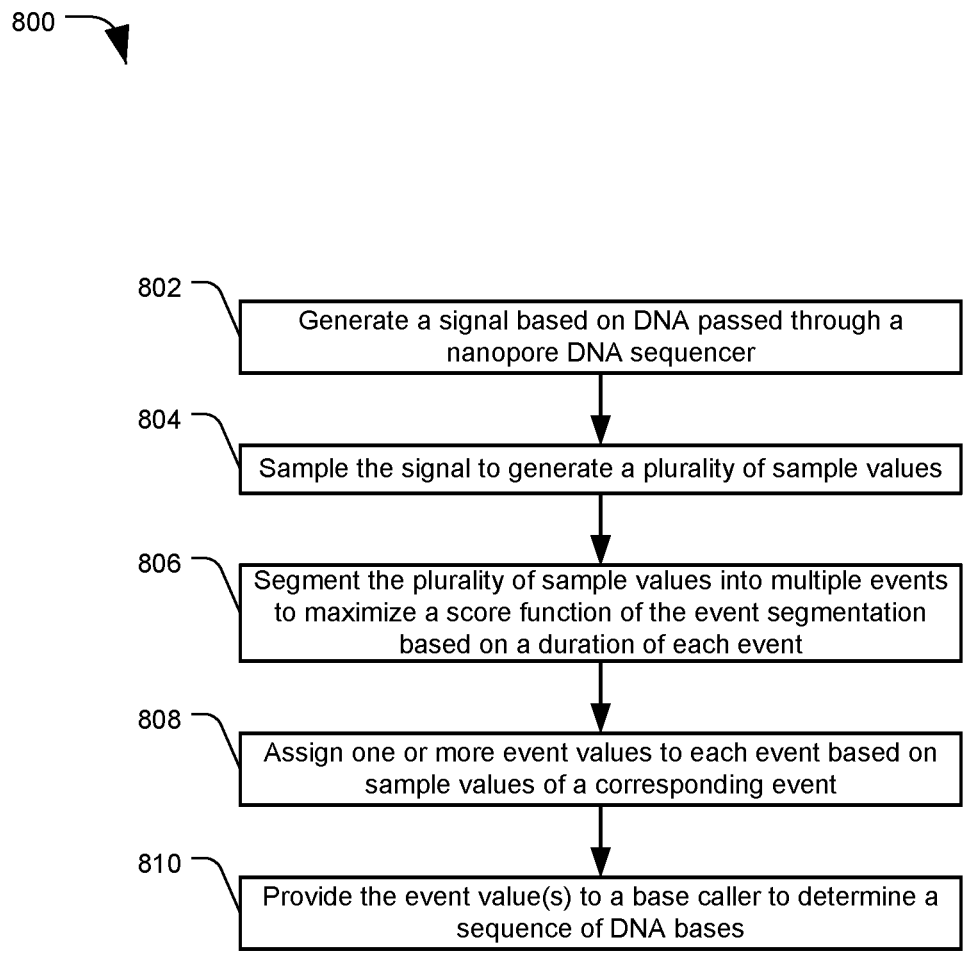
FIG. 8 is a flowchart of an example method of event timing detection for DNA sequencing, in accordance with certain embodiments of the present disclose.

FIG. 8 is a flowchart of an example method, generally designated 800, of event timing detection for DNA sequencing, in accordance with certain embodiments of the present disclose. Method 800 may be performed by one or more components of a DNA sequencing apparatus, such as the system 200 of FIG. 2.

At 802, the method 800 may include generating a signal based on DNA passed through a nanopore DNA sequencer. The nanopore DNA sequencer may include a sensor which uses a current, such as a transverse ionic current or a tunneling current, to produce a signal having characteristics based on a base of the DNA currently passing through the nanopore. At 804, the signal may be sampled to generate a plurality of sample values. For example, an analog-to-digital converter may periodically sample the analog signal to produce a digital sample value representing a voltage of the signal at the time of sampling.

The method 800 may include segmenting the plurality of sample values into multiple events to maximize a score function of the event segmentation based on a duration of each event, at 806. Different score values may be assigned to different event segmentation possibilities, based on a duration in samples for each event, and the possibilities having the highest scores may be selected to determine a most likely segmentation result.

At 808, the method 800 may include assigning one or more event values or levels to each event based on sample values for that event. The event values or levels may be provided to a base caller to determine a sequence of DNA bases based on the event values, at 810. Additional details on the proposed methodology are provided below.

To reiterate the problem statement, the goal is to find the best way to segment the given observation samples $s_n=\{s_n: n=1, \ldots, N\}$ into events. This problem can be solved by maximizing an appropriate score function of the event segmentation (e.g. to assign scores or values to different segmentation possibilities, and then to select the 'best' score, whether highest or lowest). The following definitions will be used to demonstrate the method. Let $d=\{d_k\}$ and $\lambda=\{\lambda_k\}$ denote the durations (e.g. in number of samples) and levels, respectively, of all events that make up the observation sequence. Here, d and λ may collectively be called the "event information." Let $$E_k = \left\{ j: \sum_{i<k} d_i < j \le \sum_{i \le k} d_i \right\}.$$

denote the temporal support of the k-th event. Note that $\Sigma_k d_k = N$ (e.g., the sum of the durations of all events in the sequence is equal to the total number of samples N). Next, using (1) an expression can be obtained for the log-probability of the observations given the event information is $$\log P(s|d, \lambda) = -\sum_k \sum_{n \in E_k} \left[ \frac{(s_n - \lambda_k)^2}{2\sigma^2} + \frac{1}{2}\log(2\pi\sigma^2) \right]. \qquad (2)$$

Assume that the event durations $\{d_k\}$ are independent and identically distributed (IID) and independent of the level variable $\lambda_k$ with known a priori probability distribution $P(d_k)$. Therefore, $$P(d) = \Pi_k P(d_k) \qquad (3)$$

It may not be required that $P(d_k)$ be a geometric distribution, as was the case with the SL-HMM.

A goal of the method is to estimate both event durations d and levels $\lambda$ given the observation sequence. It turns out to be sufficient to first estimate the event durations alone, provided the probability density over the level variable $\lambda$ is marginalized or maximized. The event levels can then be estimated as a post-processing step if necessary. The last step may even be unnecessary if the base-caller operates directly on the raw samples and requires only the event durations.

Different scoring functions or metrics (which may also be referred to as estimations) may be used to assign values to the potential event segmentation possibilities, and then select the segmentation result having the optimal score. Scoring algorithms may include maximum likelihood (ML) and Bayesian scoring metrics or estimations.

In instances where there is no prior information on $\lambda$, ML scoring may be used:

$$\hat{d}, \hat{\lambda} = \operatorname*{argmax}_{d,\lambda} P(s, d, \lambda) \equiv \operatorname*{argmax}_{d,\lambda} P\left( s|d, \lambda \right) P(d)$$

Since the level estimates are not important for the first step, the maximization over $\lambda$ can be pushed into the parentheses to get:

$$\hat{d} = \operatorname*{argmax}_{d} \left( \max_{\lambda} P(s|d, \lambda) P(d) \right)$$

Taking the logarithm and applying (2) and (3) provides:

$$\hat{d} = \operatorname*{argmax}_{d} \sum_k S(E_k) \qquad (4)$$

$$S(E_k) \stackrel{def}{=} -\min_{\lambda_k} \left[ \sum_{n \in E_k} \frac{(s_n - \lambda_k)^2}{2\sigma^2} \right] - \frac{d_k}{2}\log(2\pi\sigma^2) + \log P(d_k)$$

The quantity $S(E_k)$ provides the ML score associated with the k-th event supported on $E_k$. The solution to the inner minimization in (4) provides:

$$\lambda_k = \frac{1}{d_k} \sum_{n \in E_k} s_n \qquad (5)$$

e.g., the observation sample mean over event $E_k$.

Note that $P(d_k)$ in the above expressions could be any distribution. In contrast, for the SL-HMM it had to be a geometric distribution: $P(d_k=l) = p_T(1-p_T)^{l-1}$. Any quickly decaying distribution $P(d)$, or small values of $p_T$ for the geometric probability mass function (PMF), may automatically prevent over-segmentation, e.g., over-fitting the model to too many short events. Another approach may be to explicitly add a model complexity penalty such as MDL (minimum description length) or BIC (Bayesian information criterion).

In an example embodiment, noise variance $\sigma^2$ may also be unknown (in addition to information on the level variable $\lambda$) and possibly different for each event. In such cases the noise variance, $\sigma_k^2$, can be estimated along with $\lambda_k$ for each event. The ML scoring (4) provides:

$$\sigma_k^2 = \frac{1}{d_k} \sum_{n \in E_k} (s_n - \lambda_k)^2 \qquad (6)$$

and the final expression for the score:

$$S(E_k) = -d_k(1+\log 2\pi)/2 - d_k \log \sigma_k + \log P(d_k) \equiv -d_k \log (\sigma_k) + \log P(d_k). \qquad (7)$$

The term $d_k$ multiplied by a scalar can be dropped in the last step because it should not affect the maximization of the total score owing to $\Sigma_k d_k = N$ being constant. Finally, the minimum event duration can be limited, $d_k \geq d_{min}$, to avoid over-segmentation in the optimization over $\{d_k\}$.

In addition to the ML scoring function or metric described above, another scoring function that can be used is the Bayesian scoring function. If a prior probability distribution $P(\lambda)$ on $\lambda$ is known, Bayes' rule can be used to write:

$$P(d|s) \propto P(s|d)P(d) = P(d) \int_\lambda P(s|d, \lambda) P(\lambda) d\lambda$$

$$\hat{d} = \operatorname*{argmax}_{d} P(d) \int_\lambda P(s|d, \lambda) P(\lambda) d\lambda.$$

It can be shown that:

$$\hat{d} = \operatorname*{argmax}_{d} \sum_k S(E_k)$$

where $S(E_k)$ is the Bayesian score associated with the k-th event:

$$S(E_k) = -\sum_{n \in E_k} \frac{(s_n - \lambda_k)^2}{2\sigma^2} - \frac{d_k - 1}{2}\log(2\pi\sigma^2) + \log\left[ \frac{P(d_k) P^*_{d_k}(\lambda_k)}{\sqrt{d_k}} \right]. \qquad (8)$$

Here, $\lambda_k$ may be the sample mean over $E_k$ as in (5), and $P_l^*(\lambda)$ may be the probability density function (PDF) of a random variable $\lambda + \delta$ where $\lambda \sim P(\lambda)$ and $\delta \sim \mathcal{N}(0, \sigma^2/l)$ are independent. In other words, it is the convolution of the two PDFs: $P_l^*(\lambda) = P(\lambda) * \mathcal{N}(0, \sigma^2/l)$. If $P(\lambda)$ is a Gaussian mixture, then $P_l^*(\lambda)$ may also be a Gaussian mixture with all the variances increased by $\sigma^2/l$. Specifically, if $$P(\lambda) = \sum_{i=1}^{M} \pi_i \mathcal{N}(\mu_i, \gamma_i^2)$$

is the sum of M Gaussian components with component probability $\pi_i$, mean $\mu_i$ and variance $\gamma_i^2$ for $i=1, \ldots N$. Then, $$P_\ell^*(\lambda) = \sum_{i=1}^{M} \pi_i \mathcal{N}\left(\mu_i, \gamma_i^2 + \frac{\sigma^2}{\ell}\right).$$

Besides the ML and Bayesian estimation or scoring metrics, other scoring models can be applied without limiting or departing from the scope of this disclosure. Regardless of the scoring model, the event detection problem may be equivalent to maximizing the sum of individual event scores:

$$\max_d \sum_k S(E_k). \tag{9}$$

Figure 9:
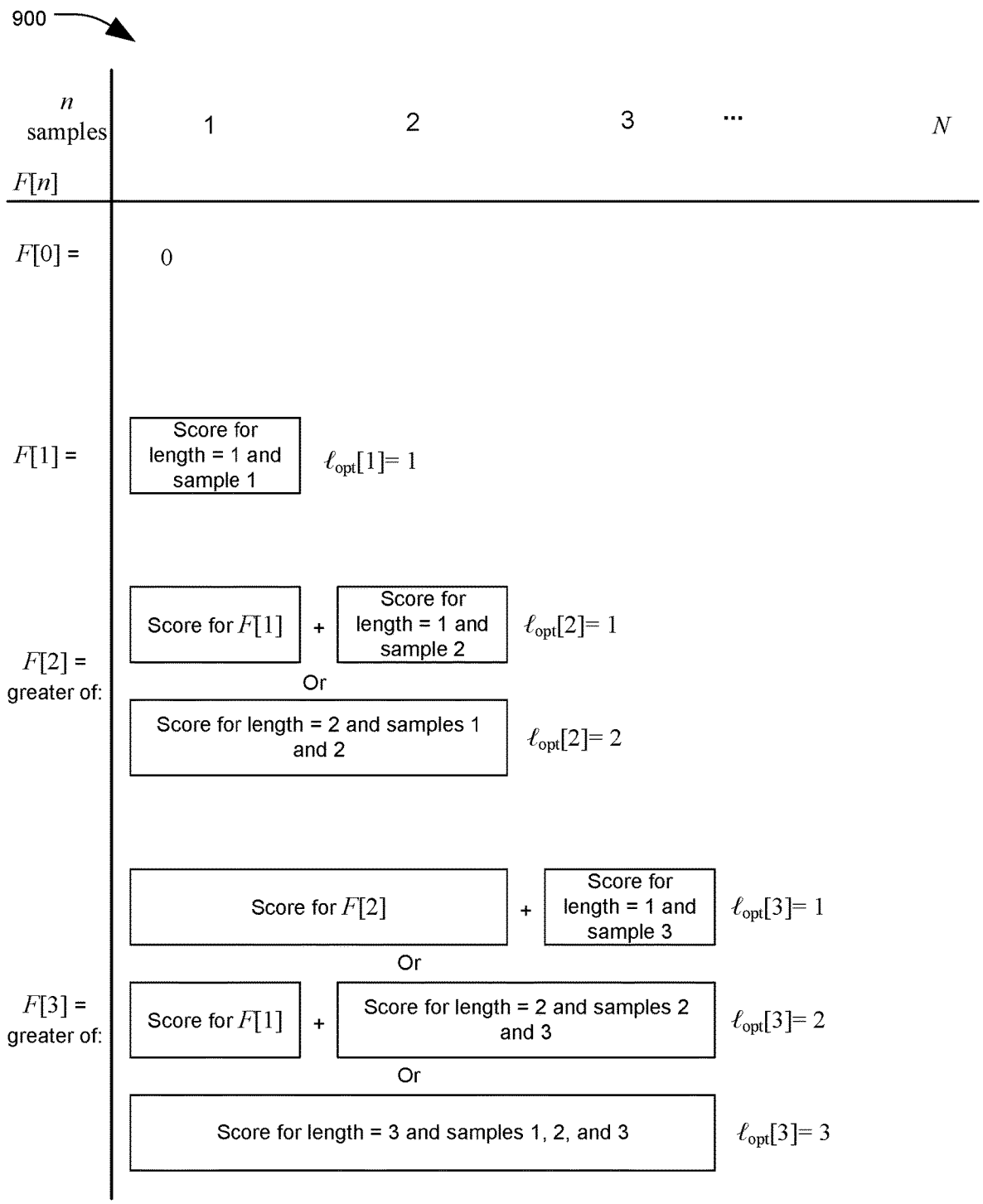
FIG. 9 is a diagram of a system configured to perform event timing detection for DNA sequencing, in accordance with certain embodiments of the present disclosure.

The application of the score maximizing operation is discussed in regard to FIG. 9.

FIG. 9 is a diagram, generally designated 900, of a system configured to perform event timing detection for DNA sequencing. In particular, FIG. 9 depicts a process for maximizing a score of a sequence of events and determining a length of each event.

One approach to solving equation (9), for determining a segmentation of events by maximizing the sum of individual event scores, can be solved using dynamic programming (DP). Let F[n] for n≤N, denote the best score for the "sub-problem of size n" whose input may be the partial observation sequence $s_1^n$ (e.g. a sequence of samples from 1 to n). Let F[0]=0 and define $E_{n,l}$ as the interval of length l ending at n, i.e., $E_{n,l}=\{j: n-l+1 \leq j \leq n\}$. For example, $E_{5,2}$ would represent an event having a length of two samples ending at sample 5, so that the event includes samples 4 and 5. Using the assumption that the dynamic program has solved all sub-problems up to size n−1, the n-th sub-problem can be solved by computing F[n] recursively as follows:

$$F[n] = \max_{1 \leq \ell \leq n} \{F[n-\ell] + S(E_{n,\ell})\}.$$

This step chooses the optimal length l for last event to maximize the sum of its score and the best score for the sub-problem of size n−l. The optimal value of l obtained for each n can be stored and tracked in an event length array $l_{opt}[n]$. This event length array can serve the "trace back" information, which can be used to determine a final optimal segmentation of events in a sequence by working backwards from the optimal length determined for the last sample of the last event. At the end of the forward pass the program should have solved all sub-problems, where "solving the sub-problem of size n" means computing the best score F[n] and the optimal final event duration $l_{opt}[n]$ for that sub-problem.

Referring to FIG. 9, the forward pass process of scoring each sub-problem will be further explained. Across the top of the diagram are listed N samples, from 1, 2, 3, . . . N, from which a currently evaluated sample n is selected, starting at sample 1. The far left column labeled F[n] represents the operation to determine a score F[n] for the sub-problem which includes all samples up to sample n. For example, the sub-problem for F[1] may consider only sample 1, while the sub-problem for F[4] may consider samples 1, 2, 3, and 4. F[0], as described above, may be assigned an initial value of 0.

The operation may first consider sample 1, at F[1]. While solving each sub-problem, it is assumed that all previous sub-problems have already been "solved" with their optimal score. For F[1], the previous sub-problem is F[0], which has a 0 score and does not affect the current sub-problem. Accordingly, all that is evaluated at F[1] is the score for an event having a length of 1 and the value of sample 1. As explained above, the scores may be based on the current sample(s) and various scoring algorithms, such as ML or Bayesian scoring. Therefore, for F[1], the appropriate score value for sample 1 and event length 1 may be stored. As the event only includes a single sample, an event length of 1 may be stored to the optimal event length array for sample 1, at $l_{opt}[1]$.

The method may then proceed to the second sub-problem, including samples 1 and 2, at F[2]. Here, the operation may need to select the highest score between multiple different scoring options, based on different possible event segmentations. A first possibility would be that sample 1 was the last sample in a first event, and that sample 2 is the first sample in a new event. The score for this possibility may be the score of F[1] added to the score generated for sample 2 as its own event of length 1. The second possibility would be that samples 1 and 2 are both from the same event. The score for this possibility may disregard the score from F[1], and instead compute the score for an event having length 2 and including both sample 1 and sample 2. The scores for these two possibilities may be compared, and the highest scoring option may be selected as the score for F[2]. If the first possibility is selected, meaning that sample 2 is the only sample in the new event, the optimal event length for $l_{opt}[2]$ would be 1. However, if the second possibility is selected, where both samples 1 and 2 are from the same event, then the optimal event length for $l_{opt}[2]$ would be 2.

The process may then proceed to F[3], where the number of possible event segmentation options has increased to three. The event length for the currently evaluated event n may be anywhere from 1 sample to n samples. The operation may consider each possibility, counting up or down from the potential event lengths. In the depicted embodiment, the first possibility is that sample 3 is the start of a new event of length 1. The score for an event of length 1 using sample 3 is calculated and added to the score of F[2]. The second possibility is that sample 3 is the second sample in an event of length 2. The score for an event of length 2 including samples 2 and 3 may be calculated, and added to the score for F[1]. The third possibility is that sample 3 is the third sample in an event including samples 1, 2, and 3. A score for such an event may be calculated. Once again the possibility with the highest score may be selected for F[3], and the corresponding event length may be stored to $l_{opt}[3]$. The process may continue until all N sub-events have been solved, and a corresponding optimal event length $l_{opt}[n]$ has been stored for each. A trace-back operation may then be performed to determine a length for each event, and accordingly the segmentation points between events, as will be discussed in regard to FIG. 10.

Figure 10:
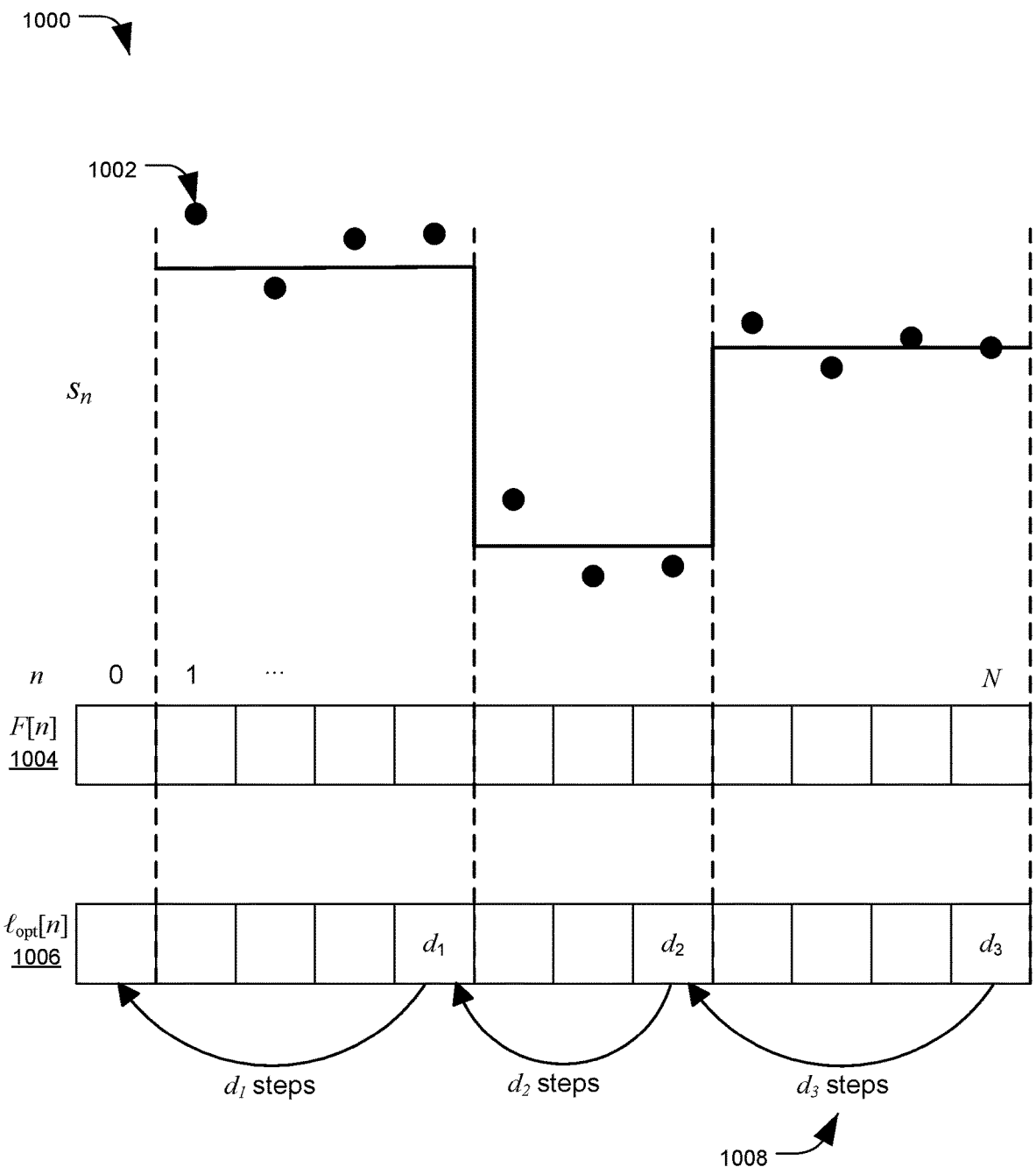
FIG. 10 is a diagram of a system configured to perform event timing detection for DNA sequencing, in accordance with certain embodiments of the present disclosure.

FIG. 10 is a diagram of a system, generally designated 1000, configured to perform event timing detection for DNA sequencing, in accordance with certain embodiments of the present disclosure. In particular, FIG. 10 depicts a process by which samples may be segmented into individual events based on run-length based scoring operations as described in regard to FIG. 9. A sequence of N samples ($s_n$) are depicted as data points or dots 1002. Two arrays may be used to store information determined during the forward scoring process described in FIG. 9. The array F[n] 1004 may store an optimal score for the sub-problem of length n. The array $l_{opt}[n]$ 1006 may store an optimal length for the event including sample n, as of that sample (e.g. the determined optimal length for the event including sample n may change as of the next sample n+1).

Once an optimal length value for each of the N samples has been stored to $l_{opt}[n]$ 1006, the next step of an event segmentation operation may be to do the trace-back to get the event durations of the optimal event segmentation. The duration of the last event, $d_3$, may be stored to $l_{opt}[N]$. The last event can be extracted or "popped off" the arrays by moving or hopping back $l_{opt}[N]$ steps (e.g. the number value of $d_3$) to the sub-problem of size $n=N-l_{opt}[n]$. The value stored to $l_{opt}[n]$, where $n=N-l_{opt}[n]$, is $d_2$, and should correspond to the duration of the penultimate event. Again, this event can be removed the process repeated, with each hop back moving to the $f_{opt}[N]$ 1006 entry storing the duration of the preceding event, until $l_{opt}[0]$ is reached. This trace-back procedure can uncover the event durations in the reverse order, starting with the last event and moving backward to the first event. Using the determined event segmentation boundaries, the samples corresponding to each event can be determined, and the values of the samples for each event may be used to determine a level corresponding to each event. For example, the sample values for a given event may be averaged, and the average sample value may be assigned as the level for that event. Alternately, the average sample value or mean sample value for a selected event may be compared to a set of pre-determined level values, and the closest pre-determined level value may be assigned to the selected event.

The following is an example set of pseudocode for an event detection dynamic programming algorithm, including both the forward scoring and the trace-back operations:

1: Initialize arrays F[0 . . . N], $l_{opt}[0 . . . N]$
2: F[0]←0
3: for n=1 . . . N do
4: $l_{opt}[n] \partial \text{argmax}_{l \geq 1} F[n-l]+S(E_{n,l})$
5: $F[n]=F[n-l_{opt}[n]]+S(E_{n,l_{opt}[n]})$
6: end for
7: n←N, d←empty stack
8: while n>0 do
9: Push $l_{opt}[n]$ into d
10: n←n−$l_{opt}[n]$
11: end while
12: OUTPUT(d)

Figure 11:
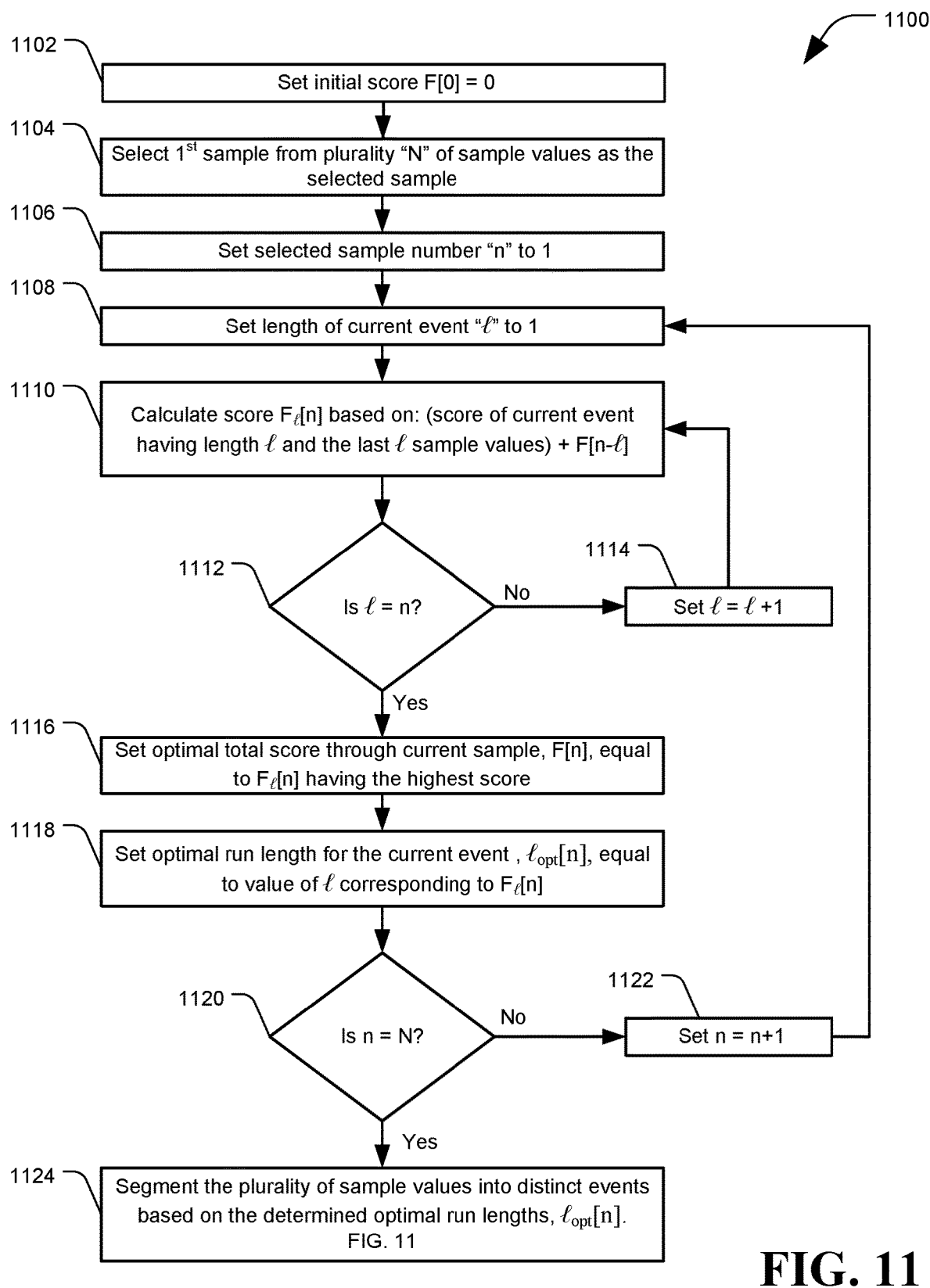
FIG. 11 is a flowchart of an example method of event timing detection for DNA sequencing, in accordance with certain embodiments of the present disclose.
Figure 12:
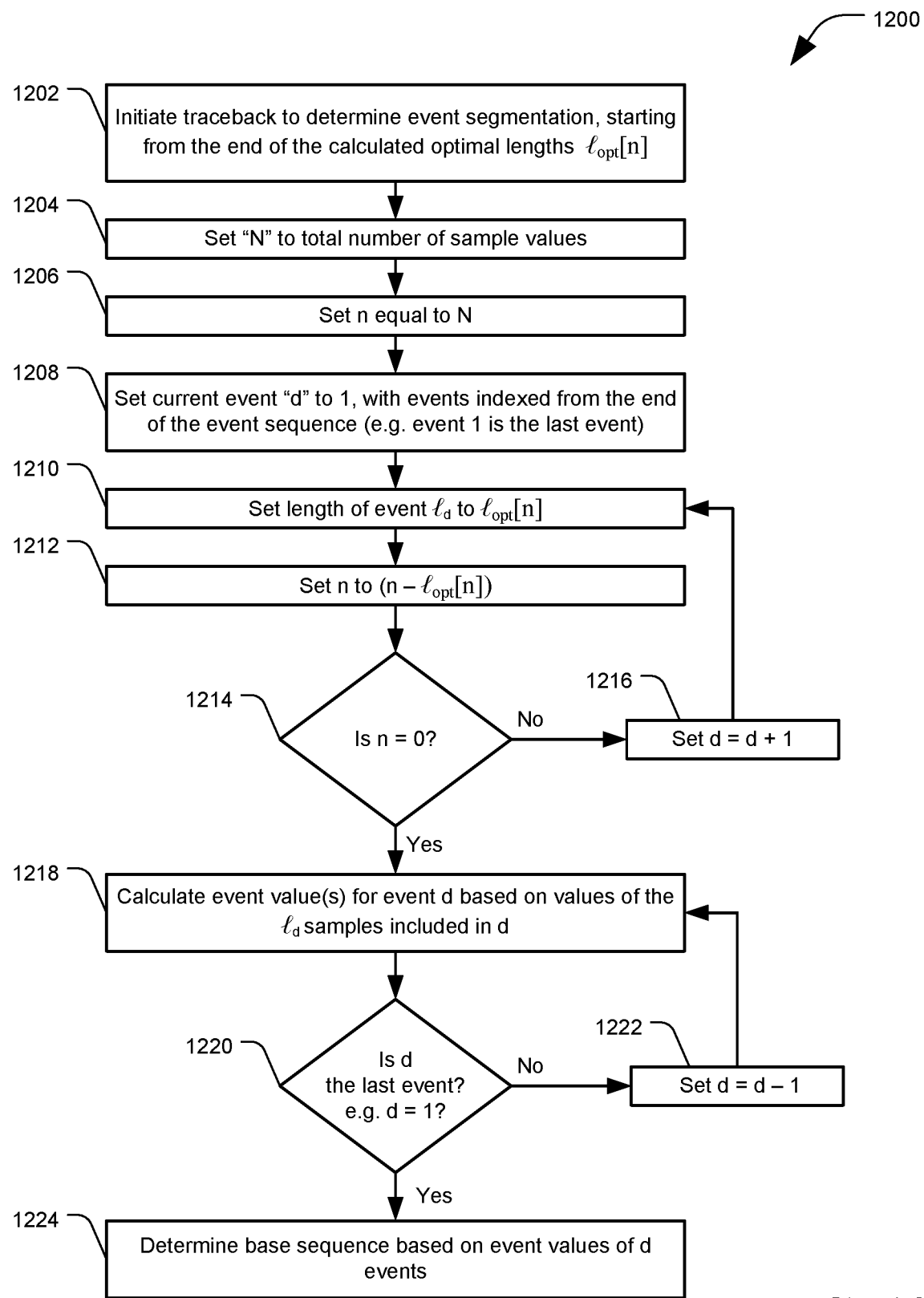
FIG. 12 is a flowchart of an example method of event timing detection for DNA sequencing, in accordance with certain embodiments of the present disclose.

The DP algorithm as presented here may have a quadratic run time unless the maximum event duration is limited. Fortunately, the algorithm has an equivalent implementation using a run-length tracking HMM (RL-HMM) as will be discussed in regard to FIG. 13. The RL-HMM also allows for limiting a number of states to a small value to effectively allow linear complexity and real-time segmentation. FIGS. 11 and 12 present flowcharts of example implementations of the dynamic programming event segmentation operation as described in regard to FIGS. 9-10.

FIG. 11 is a flowchart of an example method, generally designated 1100, of event timing detection for DNA sequencing, in accordance with certain embodiments of the present disclose. In particular, method 1100 may provide an example process for determining optimal lengths of events using a dynamic programming algorithm. Method 1100 may be performed by one or more components of a DNA sequencing apparatus, such as the system 200 of FIG. 2.

Method 1100 may include initializing an array, F[n], to store an optimal score for a sub-problem including samples 1 through n, and setting the initial score F[0] to 0, at 1102. At 1104, the method 1100 may include selecting a first sample from a plurality N of sample values as a currently selected sample, where each sample corresponds to an n value. Accordingly, the method 1100 includes setting the selected sample number "n" to 1, at 1106. A length value "l" for the current event may be initialized to 1, at 1108.

At 1110, the method 1100 may include calculating a score $F_l[n]$ based on: a computed score of the current event that has a length l and includes the last sample values, added to a maximum score for the sub-problem preceding the current event, denoted by F[n−l]. At the first sample with length 1, the value of F[1−1]=F[0], which was set to 0, so only the computed score based on sample 1 and length 1 will be used for Fi[1]. As described herein, the score may be based on applying the sample values and event length to a selected scoring algorithm, such as a ML scoring function or a Bayesian scoring function.

At 1112, a determination may be made whether l=n. If not, may be set to +1, and a next score may be calculated for an event that includes an additional sample from the last computed event, at 1110. So if n=2, first an event score may be calculated for an event with l=1 and only including sample 2 added to the score of F[1], and then may be incremented to 2, and a score may be calculated for an event with l=2 and including samples 2 and 1 added to the score F[0].

If l=n, at 1112, the method 1100 may include setting an optimal total score up through the current sample, F[n], equal to the Fe[n] having the highest score, at 1116. Next, the method 1100 may include setting the optimal run length or duration of the current event equal to the value of corresponding to the Fe[n] with the highest score, and storing the duration to an array of optimal lengths for the sub-problem n, denoted $l_{opt}[n]$, at 1118.

At 1120, a determination may be made whether n=N (e.g. whether the last sample in the set of N samples has been evaluated). If not, n may be set to n+1 to move to the next sample and the next sub-problem, at 1122. The length of the current event or sub-problem may then be set to 1, at 1108, and the scores for each potential length of the current sub-problem may then be evaluated. When n does equal N, at 1120, then the method 1100 may include segmenting the plurality of sample values into distinct events based on the determined optimal run lengths stored to $l_{opt}[n]$, at 1124. The segmentation of the samples into discrete events is described in further detail in regard to FIG. 12.

FIG. 12 is a flowchart of an example method, generally designated 1200, of event timing detection for DNA sequencing, in accordance with certain embodiments of the present disclose. In particular, method 1200 may provide an example process for implementing a trace-back operation in a dynamic programming algorithm to determine event segmentation of a sequence of samples based on determined optimal event lengths. Method 1200 may be performed by one or more components of a DNA sequencing apparatus, such as the system 200 of FIG. 2.

Method 1200 may include initiating a trace-back to determine event segmentation, starting from the last entry of the calculated optimal event length array, $l_{opt}[n]$, at 1202. To implement this, a value "N" may be set to the total number of samples in the sample sequence, at 1204, and a value "n" for a currently considered sample may be set equal to N, at 1206. At 1208, a current event "d" may be set to 1, with events indexed from the end of the event sequence (e.g. event 1 being the last event including the final sample(s)). The length of event d, denoted as fa, may be set to the value stored to $l_{opt}[n]$, at 1210. For example, this may set the length of the last event equal to a determined optimum event length for the final sample in the sequence of N samples.

Next, n may be set to the value of $(n-l_{opt}[n])$, at 1212. In this manner, the operation "hops back" a number of samples equal to the determined optimal event length at $l_{opt}[n]$, thereby skipping over all other samples in the current event. The value of n should now be set to the last sample in preceding event.

At 1214, a determination made be made whether n=0, which would indicate that all events have been segmented and no samples remain. If not, the event index d may be incremented to d+1, at 1216, and the length of this event may be set to $l_{opt}[n]$, at 1210. If n is equal to 0, at 1214, then all events have been segmented. The method 1200 may include calculating event value(s) or level(s) for the current event d based on the values of the $l_d$ samples that are included in the event d, at 1218. For example, the $l_d$ sample values may be averaged or a mean of the sample values may be obtained and used as the value or level of the event. Alternately, the event values may be used to match the event to a nearest pre-determined event value or level, which may be assigned to the event. In some embodiments, multiple values or levels may be assigned to each event, such as by also storing a number of samples included in event d, $l_d$. The calculated value(s) or level(s) may be stored to a memory, such as in an array data structure, for each event.

At 1220, a determination may be made whether d is the last event (e.g., whether d=1, indicating the final event). If not, then d may be decremented by setting it equal to d−1, at 1222, and the event value(s) for this next event may be calculated, at 1218, Once d is equal to 1, at 1220, the method may include determining a base sequence based on the event values of the d events, at 1224.

Figure 13:
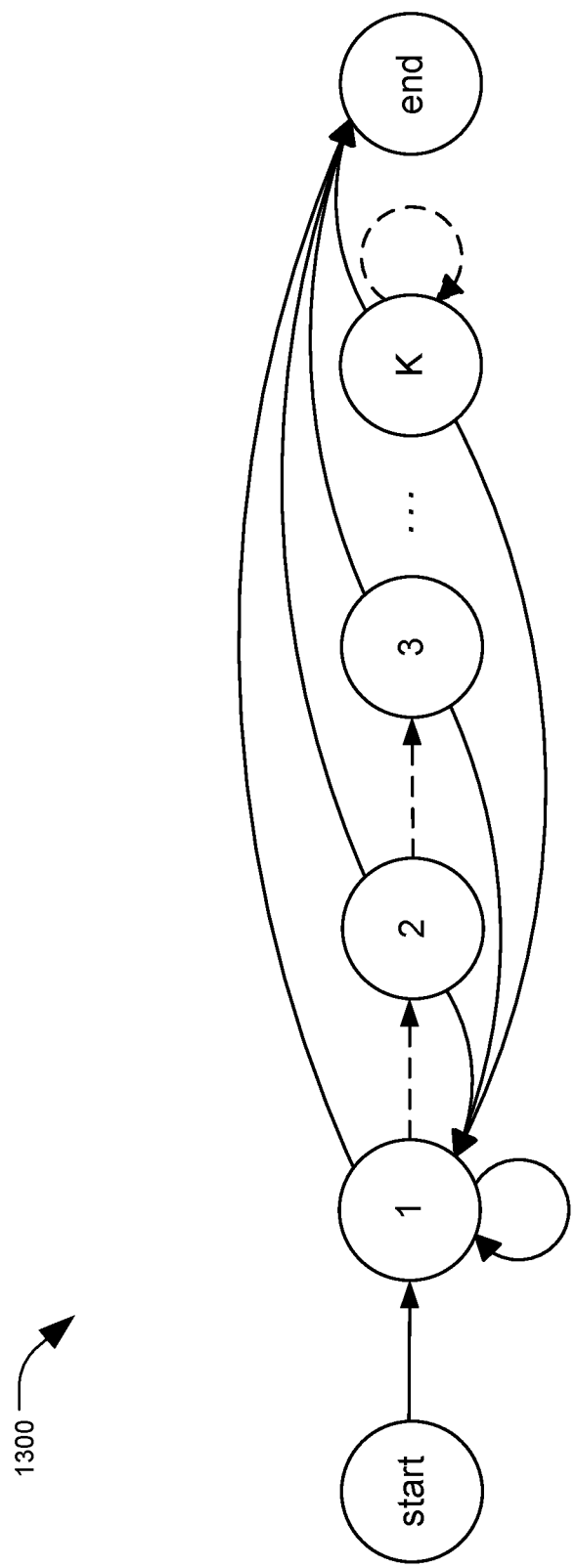
FIG. 13 is a diagram of a system configured to perform event timing detection for DNA sequencing, in accordance with certain embodiments of the present disclosure.

The dynamic program algorithm described above can be reformulated as running the Viterbi algorithm on a HMM that tracks the event durations or run lengths. FIG. 13 shows an example structure of a run-length tracking HMM, abbreviated as RL-HMM.

FIG. 13 is a diagram of a system, generally designated 1300, configured to perform event timing detection for DNA sequencing, in accordance with certain embodiments of the present disclosure. In particular, FIG. 13 depicts an example run-length-based hidden Markov model (RL-HMM) 1300 for segmenting a sequence of signal samples into separate events using a duration or run-length of each event.

Figure 14:
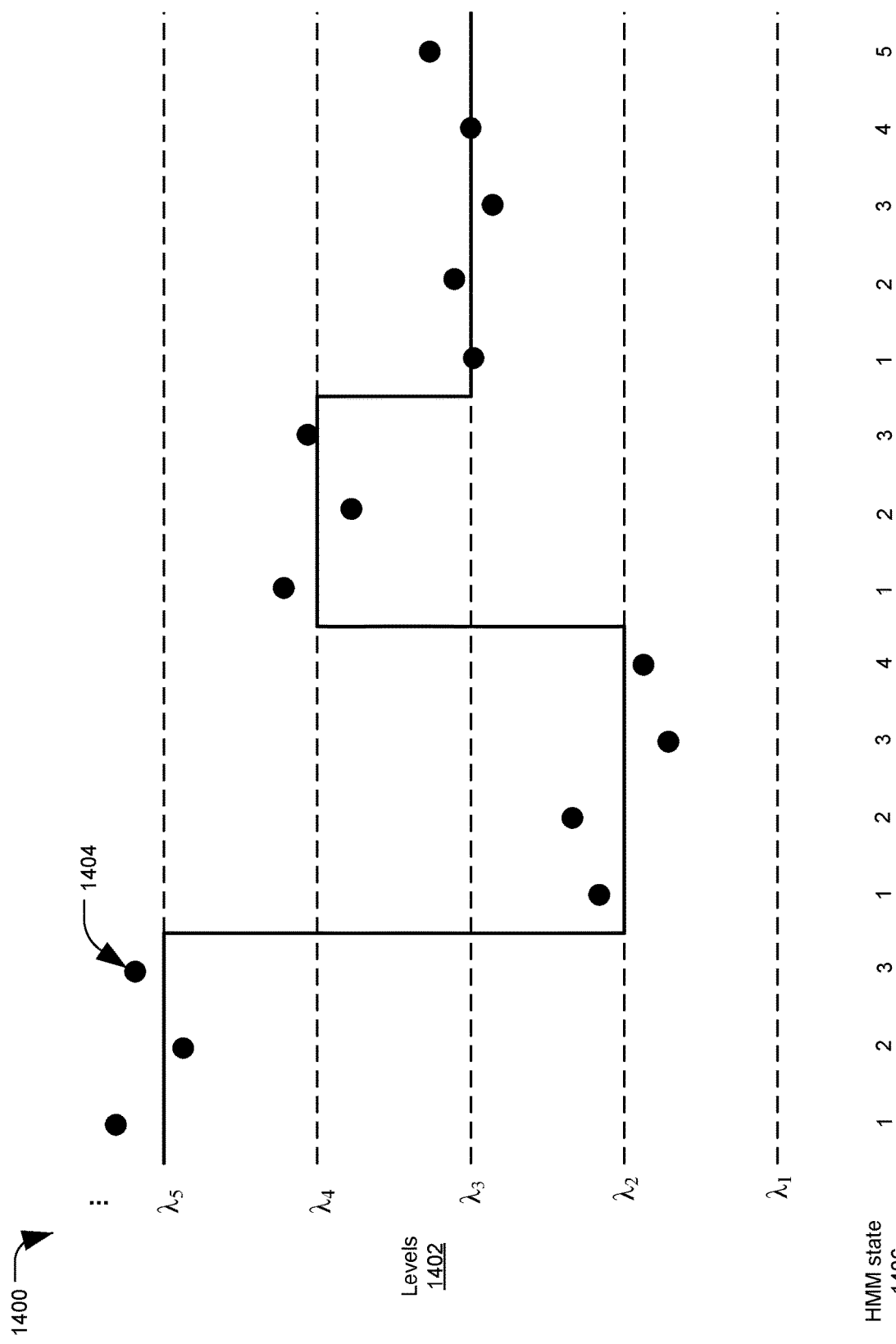
FIG. 14 is a diagram illustrating the input and output signals in event timing detection for DNA sequencing, in accordance with certain embodiments of the present disclosure.

The states of the RL-HMM 1300 may be labeled 1, 2, . . . , K. At state l≥1, the run length of current event may be l; e.g., the l most recent samples $s_{n-l+1}^n$ may make up the current event. The outgoing edges from state l may be to state l+1, representing the extension of the current run (represented by dashed lines), and to state 1, representing the end of the current event (represented by solid lines). The chain may be truncated at a large enough index K with a self-loop to handle longer runs. This does not forbid events of duration longer than K, but merely approximates the branch metric for those events. State K may be thought of as representing that the run-length is at least K. For example, the HMM may have states from 1 to 32 and then K, such that any event with a duration of 32 samples or longer will arrive at state K and continue to loop there until a new event starts or the final sample is reached and the sequence of samples ends. Special start and end states may also be included in the RL-HMM 1300 for convenience. The branch metrics in the RL-HMM may be defined as follows:

$$\beta_n(\text{start} \rightarrow 1 = \beta_n(l \rightarrow l+1) = 0 \text{ for } 1 \leq l \leq K-1$$

$$\beta_n(l \rightarrow 1) = \beta_n(l \rightarrow \text{end}) = -S(E_{n-1,l}) \text{ for } 1 \leq l \leq K$$

$$\beta_n(K \rightarrow K) = -S(E_{n,K+1}) + S(E_{n,K})$$

where $S(E_{n,\,l})$ may represent the ML, Bayesian, or other scoring function described herein for event n having length l. It can be shown that the score F[n] in the DP algorithm may equal the negative of the state metric at state "1" at time n+1 (ignoring the effect of truncation). The Viterbi algorithm may be used to compute the state sequence with the lowest accumulated path metric. This can immediately inform how to segment the sequence of samples into events. Because the RL-HMM includes a small, fixed number of branches from each state, and a potentially limited number of states (e.g. based on how many run-length states are included before reaching state K), the computational complexity can be kept low, allowing for real-time processing for event segmentation. FIG. 14 illustrates an example path (state sequence) through the RL-HMM.

FIG. 14 is a diagram of input and output signals, generally designated 1400, illustrating the event timing detection for DNA sequencing, in accordance with certain embodiments of the present disclosure. In particular, FIG. 14 shows an example path (state sequence) through a RL-HMM with an exemplary five discrete levels depicted. The state sequence may correspond to a RL-HMM such as the one depicted in FIG. 13.

The levels 1402 may be identified as $\lambda_1$ through $\lambda_5$, with additional levels not shown. Each level 1402 may correspond to a signal level or average value of the samples in a given event, and there may be a large number of levels 1402, or a continuous level range, into which the events may be categorized. The dots 1404 may represent individual samples taken from the measured signal, with their y-position on the chart indicating the signal value of that particular sample. The solid line may indicate which levels 1402 that each sequence of samples 1404 correspond to.

The HMM states 1406 may represent a duration of the current event, based on a number of samples in the event. A new event may begin whenever the state index 1406 is reset to 1. The HMM state 1406 for a given event will increase for each new sample in the event, until a new event begins and the HMM state 1406 resets to 1. As can be seen, the first event include three samples, and so the HMM state 1406 increases from 1, to 2, to 3, and then resets to 1 at the start of the next event. Example methods for implementing a RL-HMM based event segmentation operation are described in regard to FIGS. 15 and 16.

Figure 15:
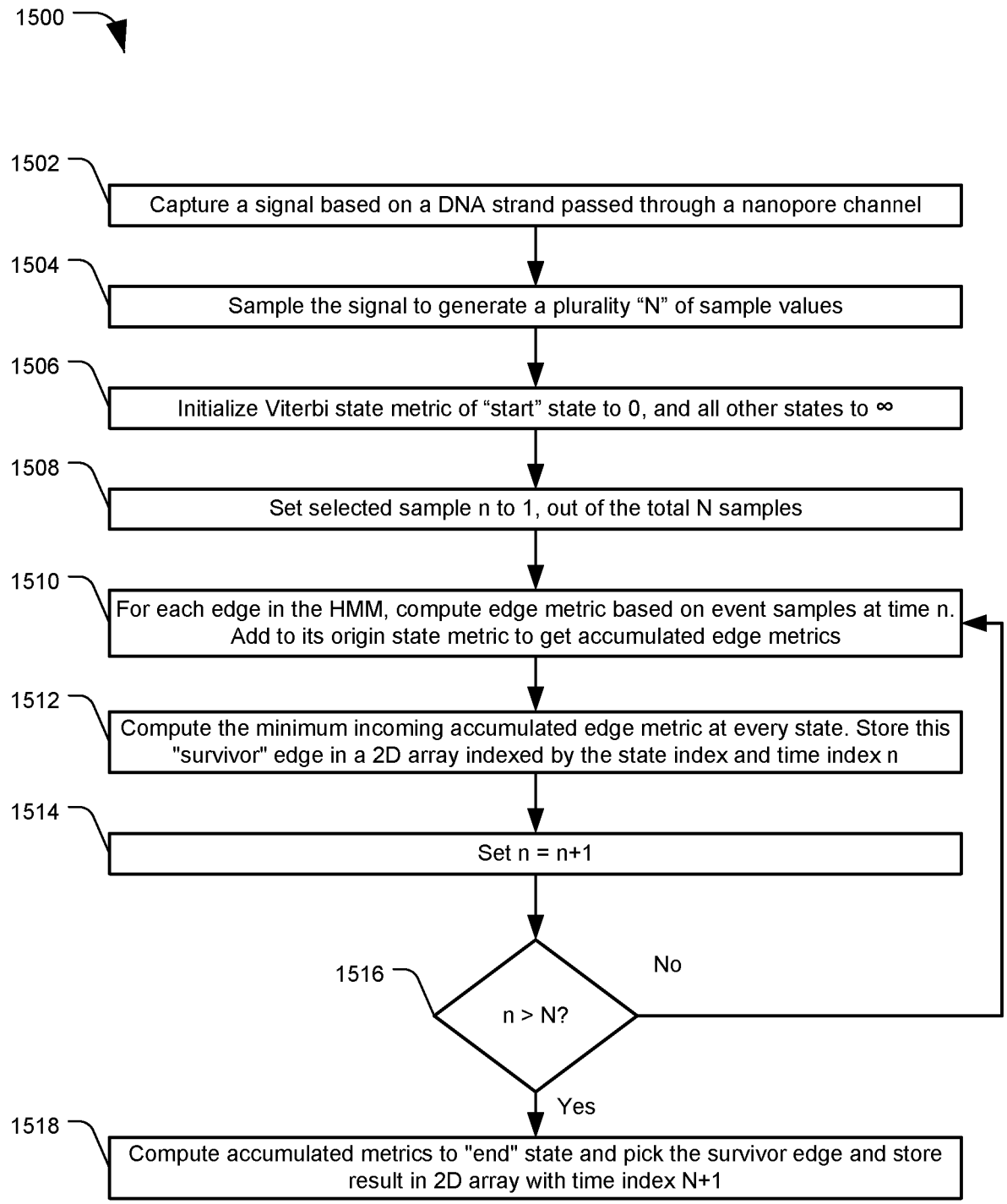
FIG. 15 is a flowchart of an example method of event timing detection for DNA sequencing, in accordance with certain embodiments of the present disclose.

FIG. 15 is a flowchart of an example method, generally designated 1500, of event timing detection for DNA sequencing, in accordance with certain embodiments of the present disclose. In particular, method 1500 may provide an example process for determining event run lengths based on a RL-HMM. Method 1500 may be performed by one or more components of a DNA sequencing apparatus, such as the system 200 of FIG. 2.

Method 1500 may include capturing a signal based on a DNA strand passed through a nanopore channel, at 1502. The signal may then be sampled to generate a plurality "N" of sample values, at 1504. Next, a Viterbi state metric of a "start" state may be set to 0, and all other states may be initialized to Do (infinity), at 1506. A value of n may be set to 1, representing a selected sample from the plurality of N samples, at 1508.

Once the values have been initialized, the method 1500 may include computing, for each edge in the RL-HMM, an edge metric based on event samples at time n. At state € these may be the € most recent samples ending at the n-th sample. Then the edge metric can be added to the origin state metric of the edge to get accumulated edge metrics, at 1510. At the beginning of the operation, every state but "start" may be initialized to ∞ and so most of the accumulated edge metrics will be ∞. At 1512, the method 1500 may include computing the minimum incoming accumulated edge metric at every state. The "survivor" minimum edge metric may be stored to a 2-dimensional array indexed by the state index and a time index represented by n.

The method 1500 may then include incrementing n, at 1514. At 1516, a determination may be made whether n>N (e.g. whether the final sample has been evaluated). If not, the method 1500 may include computing the edge metric for each edge in the HMM at the new time n, 1510. If n>N, then the method 1500 may include computing (e.g. via the Viterbi algorithm) the accumulated path metrics to the "end" state and picking the survivor (minimum) edge, at 1518. The result may be stored to a 2D array with time index N+1. In this manner, an optimal path from the start state to the end state at the final sample may be generated, which may include information on an optimal length for each event. The trace-back procedure to segment the events using the RL-HMM model is described in regard to FIG. 16.

Figure 16:
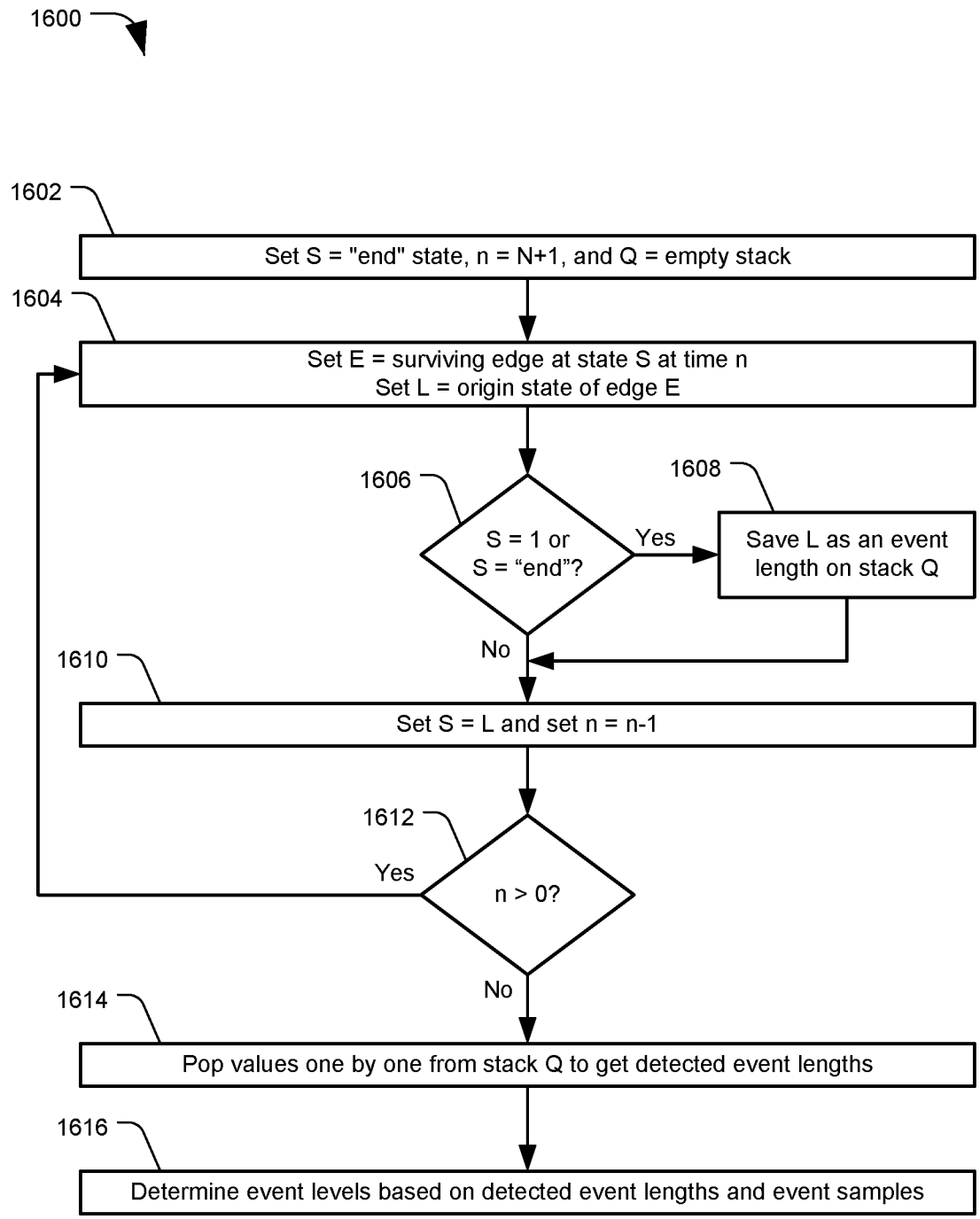
FIG. 16 is a flowchart of an example method of event timing detection for DNA sequencing, in accordance with certain embodiments of the present disclose.

FIG. 16 is a flowchart of an example method, generally designated 1600, of event timing detection for DNA sequencing, in accordance with certain embodiments of the present disclose. In particular, method 1600 may provide an example process for event segmentation based on the event run lengths determined via a RL-HMM, as described for FIG. 15. Method 1600 may be performed by one or more components of a DNA sequencing apparatus, such as the system 200 of FIG. 2.

At 1602, the method 1600 may include setting a current state value "S" to the "end" state, setting a value of a currently selected sample or time value "n" equal to N+1 (one more than the number of samples in a sequence of N samples, as the "end" state may occur after the final sample), and initializing an empty stack data structure "Q" to store event lengths. The method 1600 may include setting a selected edge variable "E" equal to the surviving (e.g. minimum-value) edge terminating at state S at time n, and setting a length value "L" for the current event to the origin state index of edge E, at 1604. The values, as used herein, may be obtained from a 2D array populated during the method of FIG. 15, for example.

A determination may then be made whether the current state S is equal to 1 or the "end" state, at 1606. If so, then the current state S at time n may have been the beginning of a new event or the end of the sample buffer, and therefore the previous state, L, may correspond to the length of the previous event. Accordingly, the method may include saving the value of L as an event length on stack Q, at 1608. Once the value of L is stored to Q at 1608, or if S was not equal to 1 at 1606, the method 1600 may include setting S=L and decrementing n, at 1610. In this manner the method continues to "walk backward" through the RL-HMM states for each previous sample n. At 1612, a determination may be made whether n>0, in order to determine whether the first sample has been reached. If n is greater than 0, there are additional samples to work through, and so the method may loop to setting a new value for E and L, at 1604. If n is not greater than 0, at 1612, the method 1600 may include "popping" or removing the values one by one from the stack Q in order to obtain the detected event lengths, at 1614. At 1616, the method 1600 may include determining event levels from the DNA strand based on the detected event lengths and the corresponding event samples. In some embodiments, a DNA base sequence may be determined based on the event levels.

A RL-HMM-based event segmentation approach may offer several advantages over a SL-HMM-based event detection approach:

RL-HMM works efficiently for large and even continuous level sets. When using the ML scoring function, no additional information about the levels is needed at all. This may be particularly useful when trying to perform (blind) event segmentation on unlabeled data. With SL-HMM it may be necessary to know the set of possible levels beforehand.

The total computational complexity of the RL-HMM implementation may be O(KN) where N is the observation sequence length and K is the maximum state index. In practice K of three times the average event duration works well (e.g. K≈32 for the *E. coli* data). This complexity compares favorably to the SL-HMM whose complexity may be $O(NL^2)$, where the number of discrete levels L may typically be a very large number.

RL-HMM allows for the use of distributions for event duration other than the geometric distribution. In practice we can estimate the distribution can be estimated from training data, and that it may often not be geometrically distributed.

Figure 17:
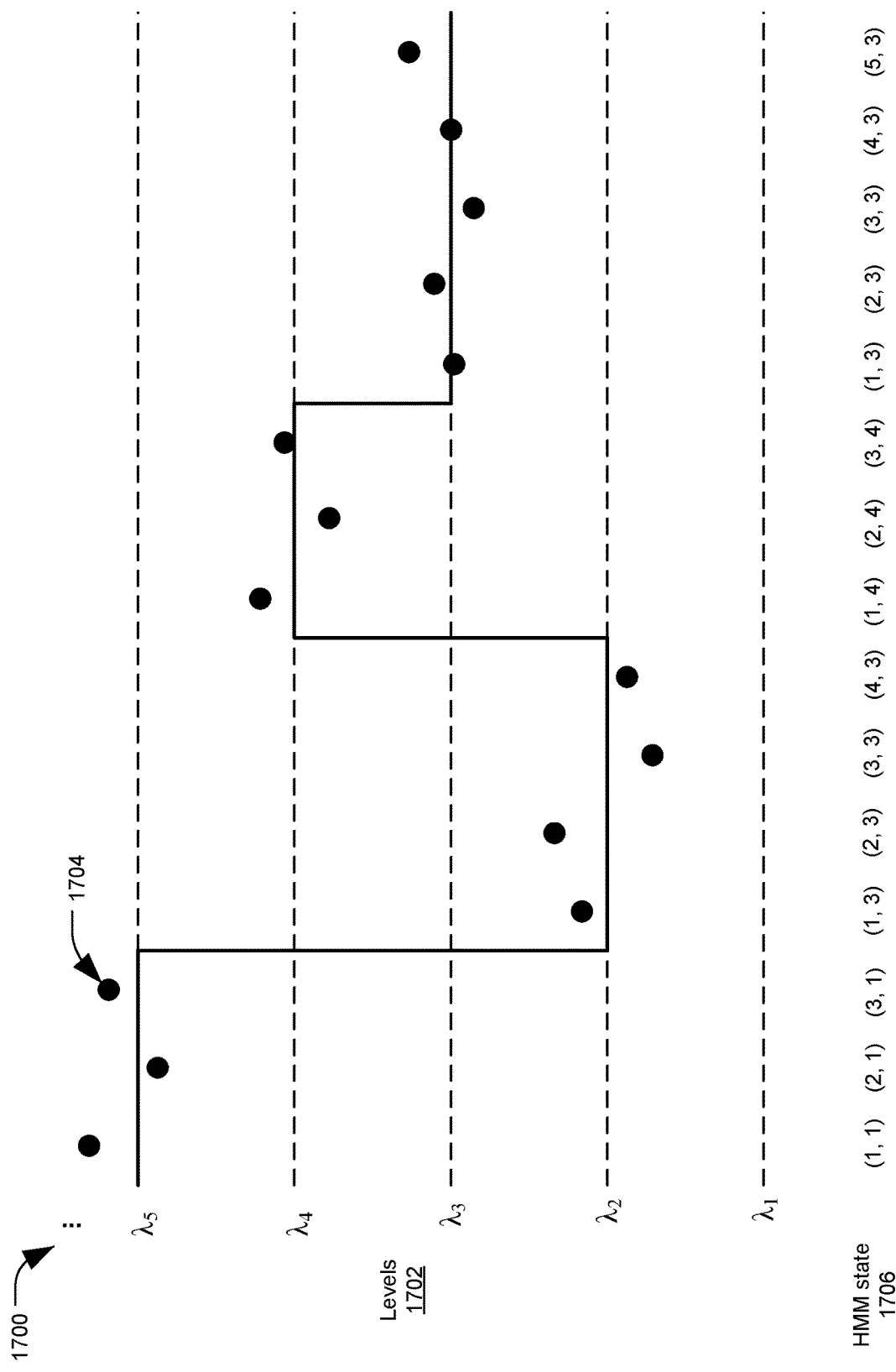
FIG. 17 is a diagram illustrating the input and output signals in event timing detection for DNA sequencing, in accordance with certain embodiments of the present disclosure.

Turning now to FIG. 17, situations in which additional factors are considered for event durations are discussed. FIG. 17 is a diagram of input and output signals, generally designated 1700, illustrating the event timing detection for DNA sequencing, in accordance with certain embodiments of the present disclosure. In particular, FIG. 17 shows an example path (state sequence) through a RL-HMM with an exemplary five discrete levels 1702 depicted, and in which the duration of a previous event is also factored for the current event.

So far, the discussion has assumed that the event durations $d_k$ form an independent and identically distributed (IID) sequence. But, the duration of an event may depend on the complex dynamics of DNA translocation through the nanopore channel. The durations of neighboring events may therefore be correlated, depending on the exact device architecture. Accordingly, the run length-tracking HMM may be generalized to handle correlated event durations.

An example way to introduce correlations in the event durations may be to model the duration as a Markov process. E.g., $$P(d) = P(d_1) \Pi_{k \geq 2} P(d_k | d_{k-1}) \quad (10)$$

All of the previous analysis on the RL-HMM can be extend to this case by replacing $P(d_k)$ with $P(d_k|d_{k-1})$ in the ML and Bayesian scoring functions (4) and (8). By doing so, the scores (except for the first event) may now depend on pairs of neighboring events. The event detection problem can be solved by maximizing the total score expressed as $$\max_d \left[ S(E_1) + \sum_{k \geq 2} S(E_k, E_{k-1}) \right] \quad (11)$$

where $E_k$ is the support of the k-th event, and the score $S(E_k, E_{k-1})$ depends on a pair of consecutive events due to the Markov dependence of the event durations. The maximization (11) contains scores of event pairs, but is otherwise very similar to the problem (9). As described below, it can be solved using a dual RL-HMM which tracks the durations of the two most recent events. In some embodiments, the run lengths of more than the two most recent events may be tracked in exchange for added complexity of the HMM.

For a dual RL-HMM, the HMM state may be a pair of integers (l,l') where € may be the current event duration, and l' may be the previous event duration. The state (l,l') may have an outgoing edge to (l+1,l') which increments the current event duration, and an edge to (1,l) which starts the next event. As before, each of the two event durations can be tracked up to K samples. This can result in an HMM with $K^2$ states: (l,l') for $1 \leq l, l' \leq K$. The Viterbi branch metrics can be defined as follows:

$$\beta(\text{start} \to (1,l')) = \beta_n((l,l') \to (l+1,l')) = 0$$

$$\beta_n((l,l') \to (1,l)) = \beta_n((l,l') \to \text{end}) = -S(E_{n-1,l}, E_{n-1-l,l'}).$$

The overall computational complexity may be O ($K^2N$), which is still linear in N but with a larger constant factor of $K^2$. FIG. 17 shows a typical path (state sequence) output by the Viterbi detector of a dual run length HMM for the hypothetical observation samples shown as dots 1704. As with FIG. 14, five discrete signal levels 1702 are depicted, although there may be significantly more levels or there may be fewer levels. The MEW state 1706 for each sample 1704 reflects both the current run length of the current event as the first number l, and the run length of the previous event as the second number l' (which, for the first event, may default to "1"). The first event ends up having a run length of 3 samples, which becomes the value of l' for the second event MEW states.

In summary, nanopore DNA sequencing may be a single molecule sequencing technology that promises low-cost, high-throughput DNA sequencing for medical applications, DNA-based data storage, and other potential fields. A single strand of DNA from the sample may be made to pass through a nanopore channel using electrophoresis. The raw signal measured by the device may be an oversampled ionic or tunneling current that changes depending on the base sequence in the DNA strand.

In this disclosure, the problem of event detection, which is the segmentation of the sampled current signal into events corresponding to individual bases transiting through the nanopore channel, has been addressed. Event detection and segmentation may be a precursor step to the base-calling problem, which determines the actual base sequence in the DNA strand.

This disclosure addresses a simple HMM-based event detector that tracks the signal levels (SL-HMM). While this method works well if there are only a few discrete levels, it turns out to be expensive to implement for large level sets such as for a data set for *E. coli* DNA. Accordingly, the disclosure proposes a novel dynamic programming algorithm whose implementation is a reduced state run length tracking HMM (RL-HMM) based event detector. The RL-HMM has been shown to be provably equivalent to the SL-HMM for discrete level sets, but can generalize and out-perform it many ways:

RL-HMM works efficiently for very large or even continuous level sets, while the SL-HMM may only work for discrete level sets.

RL-HMM can have a much lower implementation complexity than SL-HMM for large level sets. SL-HMM may have an implementation complexity of $O(NL^2)$ where N may be the input sequence length and L may be the number of levels. In contrast, RL-HMM may have a complexity of O(NK) operations where K is the maximum state index; K=32 may work well for typical nanopore data, even with a continuous level set model.

RL-HMM can work for any probability distribution for the event duration. For a slightly larger complexity of $O(NK^2)$, RL-HMM can be adapted to model Markov dependence in durations of consecutive events, but SL-HMM can only model IID and geometrically distributed durations.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Moreover, although specific embodiments have been illustrated and described herein, it should be appreciated that any subsequent arrangement designed to achieve the same or similar purpose may be substituted for the specific embodiments shown.

This disclosure is intended to cover any and all subsequent adaptations or variations of various embodiments. Combinations of the above embodiments, and other embodiments not specifically described herein, will be apparent to those of skill in the art upon reviewing the description. Additionally, the illustrations are merely representational and may not be drawn to scale. Certain proportions within the illustrations may be exaggerated, while other proportions may be reduced. Accordingly, the disclosure and the figures are to be regarded as illustrative and not restrictive.

What is claimed is:

1. A method comprising:
    generating a signal based on a DNA (deoxyribonucleic acid) strand passed through a nanopore sensor;
    sampling the signal to generate a plurality of sample values;
    detecting one or more event boundaries based on the sample values, an event representing a movement of a single DNA base of the DNA strand through the nanopore sensor, including:
        segmenting the plurality of sample values into multiple events by applying the plurality of sample values to a dynamic programming algorithm configured to calculate an optimal score at each sample based on potential run lengths for a latest event including the sample, store a run length corresponding to the optimal score for each sample, and perform a traceback operation to segment the plurality of sample values into the multiple events based on the run length stored for a last sample in each event, starting with a last sample in the plurality of sample values;
        assigning an event value to a selected event from the multiple events based on sample values of the selected event; and
    providing the event value to a base caller to determine a sequence of DNA bases.

2. The method of claim 1 further comprising:
    segmenting the plurality of sample values into the multiple events by applying a scoring metric based on the run length for each event, the run length corresponding to a number of sequential samples values in an event.

3. The method of claim 2 further comprising the scoring metric includes maximum-likelihood estimation.

4. The method of claim 2 further comprising the scoring metric includes Bayesian estimation.

5. The method of claim 2 further comprising:
segmenting the plurality of samples values into the multiple events includes:
applying the plurality of sample values to a hidden Markov model (HMM) having:
states which track a number of consecutive samples in an event;
edge values between states based on the plurality of sample values applied to the scoring metric;
applying a Viterbi algorithm to the HMM to determine a state sequence having a least accumulated path metric; and
segmenting the plurality of sample values into the multiple events based on the determined state sequence.

6. The method of claim 5 further comprising:
the HMM includes a dual run-length HMI which tracks durations of two most recent events; and
applying the scoring metric is based on run lengths of the two most recent events.

7. The method of claim 1 further comprising:
detecting one or more event levels based on the sample values, an event level corresponding to a readout signal level of the sample values.

8. An apparatus comprising:
a signal processing channel circuit configured to:
generate a signal based on a DNA (deoxyribonucleic acid) strand passed through a nanopore sensor;
sample the signal to generate a plurality of sample values;
detect one or more event boundaries based on the sample values, an event representing a movement of a single DNA base of the DNA strand through the nanopore sensor, including:
segment the plurality of sample values into multiple events by applying the plurality of sample values to a dynamic programming algorithm configured to calculate an optimal score at each sample based on potential run lengths for a latest event including the sample, store a run length corresponding to the optimal score for each sample, and perform a trace-back operation to segment the plurality of sample values into the multiple events based on the run length stored for a last sample in each event, starting with a last sample in the plurality of sample values;
assign an event value to a selected event from the multiple events based on sample values of the selected event; and
provide the event value to a base caller to determine a sequence of DNA bases.

9. The apparatus of claim 8 comprising the circuit further configured to:
segment the plurality of sample values into the multiple events by applying a scoring metric based on the run length for each event, the run length corresponding to a number of sequential samples values in an event.

10. The apparatus of claim 9 further comprising the scoring metric includes maximum-likelihood estimation.

11. The apparatus of claim 9 further comprising the scoring metric includes Bayesian estimation.

12. The apparatus of claim 9 further comprising:
segmenting the plurality of samples values into the multiple events includes:
applying the plurality of sample values to a hidden Markov model (HMM) having:
states which track a number of consecutive samples in an event;
edge values between states based on the plurality of sample values applied to the scoring metric;
applying a Viterbi algorithm to the HMM to determine a state sequence having a least accumulated path metric; and
segmenting the plurality of sample values into the multiple events based on the determined state sequence.

13. The apparatus of claim 12 further comprising:
the HMM includes a dual run-length HMI which tracks durations of two most recent events; and
the circuit further configured to apply the scoring metric based on run lengths of the two most recent events.

14. The apparatus of claim 8 comprising the circuit further configured to:
detect one or more event levels based on the sample values, an event level corresponding to a readout signal level of the sample values.

15. A memory device storing instructions that, when executed by a processor, cause the processor to perform a method comprising:
generating a signal based on a DNA (deoxyribonucleic acid) strand passed through a nanopore sensor;
sampling the signal to generate a plurality of sample values;
detecting one or more event boundaries based on the sample values, an event representing a movement of a single DNA base of the DNA strand through the nanopore sensor, including:
segmenting the plurality of sample values into multiple events by applying the plurality of sample values to a dynamic programming algorithm configured to calculate an optimal score at each sample based on potential run lengths for a latest event including the sample, store a run length corresponding to the optimal score for each sample, and perform a trace-back operation to segment the plurality of sample values into the multiple events based on the run length stored for a last sample in each event, starting with a last sample in the plurality of sample values;
assigning an event value to each event from the multiple events based on sample values of a corresponding event; and
providing the event values to a base caller to determine a sequence of DNA bases.

16. The memory device of claim 15, storing instructions causing the processor to perform the method further comprising:
segmenting the plurality of sample values into the multiple events by applying a scoring metric based on the run length for each event, the run length corresponding to a number of sequential samples values in an event.

17. The memory device of claim 16 further comprising the scoring metric is selected from a list including a maximum-likelihood scoring metric and a Bayesian scoring metric.

18. The memory device of claim 16, storing instructions causing the processor to perform the method further comprising:
segmenting the plurality of samples values into the multiple events includes:
applying the plurality of sample values to a hidden Markov model (HMM) having:
states which track a number of consecutive samples in an event;

edge values between states based on the plurality of sample values applied to the scoring metric;

applying a Viterbi algorithm to the HMM to determine a state sequence having a least accumulated path metric; and segmenting the plurality of sample values into the multiple events based on the determined state sequence.

19. The memory device of claim 18 further comprising:

the HMM includes a dual run-length HMI which tracks durations of two most recent events; and the memory device storing instructions that cause the processor to perform the method further comprising:

applying the scoring metric based on run lengths of the two most recent events.

20. The memory device of claim 15, storing instructions causing the processor to perform the method further comprising:

detecting one or more event levels based on the sample values, an event level corresponding to a readout signal level of the sample values.

\* \* \* \* \*